United States Patent [19]

Barnes

[11] Patent Number: 5,240,831
[45] Date of Patent: Aug. 31, 1993

[54] METHODS AND COMPOSITIONS FOR THE EXPRESSION OF BIOLOGICALLY ACTIVE EUKARYOTIC CYTOCHROME P450S IN BACTERIA

[75] Inventor: Henry J. Barnes, Dallas, Tex.

[73] Assignee: Board of Regents, The University of Texas, Austin, Tex.

[21] Appl. No.: 640,473

[22] Filed: Jan. 10, 1991

[51] Int. Cl.$^5$ ............... C12N 15/00; C12N 15/53; C12N 15/67; C12N 15/70

[52] U.S. Cl. ............... 435/69.1; 435/172.3; 435/252.3; 435/252.33; 435/320.1; 435/189; 935/6; 935/10; 935/14; 935/44; 935/45; 935/72; 935/73

[58] Field of Search ............... 435/69.1, 172.3, 252.33, 435/320.1; 536/27

[56] References Cited

U.S. PATENT DOCUMENTS

| | | | |
|---|---|---|---|
| 4,766,068 | 8/1988 | Oeda et al. | 435/68 |
| 5,045,471 | 9/1981 | Miller | 435/320.1 |

FOREIGN PATENT DOCUMENTS

| | | |
|---|---|---|
| 0360361 | of 0000 | European Pat. Off. |
| WO89/1096-31 | 11/1989 | PCT Int'l Appl. |
| 91/03561 | of 0000 | World Int. Prop. O. |

OTHER PUBLICATIONS

White, P. C., et al., 1984 Proceedings of the National Academy of Sciences USA, 81:1986-1990.
Evans, L. T., et al., 1986, Proceedings of the National Academy of Sciences USA 83:6387-6391.
Navhi; L. O., et al., 1988, Molecular and Cellular Biochemistry 79(1): 63-72 (abstract).
Porter, T. P., et al., 1987, Archives of Biochemistry and Biophysics 244(1):353-367.
Mittal, S., et al., 1988, Archives of Biochemistry and Biophysics, 264(2):383-391.
Koga, H., et al., 1985, Biophysical and Biochemical Research Communications 130(1):412-417.
Porter et al., Proceedings of the VIIIth International Symposium on Microsomes and Drug Oxidations, Karolinska Institutet, Stockholm, Jun. 25-29, 1990, Eds. M. Ingelman-Sundberg, J-Å. Gustafsson, S. Orrenius, Abstract L-35.
Feyereisen et al., PNAS, 86:1465-1469, 1989.
Andersson et al., J. Bio. Chem., 264(14):8222-8229, 1989.
Cullin and Pompon, Gene, 65:203-217, 1988.
Corbin et al., PNAS, 85:8948-8952, 1988.
Hardwick et al., J. Biol. Chem., 262(2):801-810, 1987.
Chua et al., PNAS, 84:7193-7197, 1987.
Zuber et al., J Biol Chem, 261(5):2475-2482, 1986.
Yoshioka et al., J Biol Chem, 261(9):4106-4109, 1986.
Gonzalez et al., J. Bio. Chem., 260(12):7435-7441, 1985.
Morohashi et al., PNAS, 81:4647-4651, 1984.
Yabusaki et al., Nuc Acid Res., 12(6):2929-2938, 1986.
Fujii-Kuriyama et al., PNAS, 79:2793-2797, 1982.
McCarthy and Gualerzi, Trends Genetics, 6(3):78-85, 1990.
Gold and Stormo, Methods in Enzymology, 185:89-93, 1990.
DeBoer and Hui, Methods in Enzymology, 185:103-114, 1990.
Chen and Inouye, Nucl Acid Res, 18(6):1465-, 1990. (Abstract only).

(List continued on next page.)

*Primary Examiner*—Robert A. Wax
*Assistant Examiner*—William W. Moore
*Attorney, Agent, or Firm*—Arnold, White Durkee

[57] ABSTRACT

Disclosed are methods and compositions for effecting bacterial expression of eukaryotic cytochrome P450 enzymes in a biologically active form. Particular embodiments involve the expression of eukaryotic cytochrome $P450_{17\alpha}$-hydroxylase which is expressed in large amounts in an *E. coli* host in a biologically active form without the need for coexpression or admixture of a cytochrome P450 reductase. Techniques are disclosed for effecting improved bacterial expression which are proposed to be useful in connection with all eukaryotic cytochrome P450 enzymes which one may desire to express in bacterial hosts such as *E. coli* and others.

49 Claims, 5 Drawing Sheets

OTHER PUBLICATIONS

Gold and Stormo, 'E. coli and Salmonella typhimerium Cellular and Molecular Biology', American Society for Microbiology, Washington, D.C., Ed. F. C. Weidhardt, 1987, pp. 1302–1307.

Bachmair et al., Science, 234:179–, 1988. (Abstract only).

Gren, Biochimie, 66:1–29, 1984.

Stormo et al., Nucl Acid Res, 10(9):2971–2975, 1982.

Platt, Ann Rev Biochem, 55:339–372, 1986.

Hawley and McClure, Nucl Acid Res, 11(8):2237–2255, 1983.

Rosenberg and Court, Ann Rev Genet, 13:319–353, 1979.

Kawasaki, PCR Protocols: A Guide to Methods and Applications, Academic Press, Inc., 1990, pp. 21–27.

Higuchi et al., Nucl Acid Res, 16(15):7351–7367, 1988. (Abstract only).

Dialog Search References.

Hu & Chung, Mol. Endocrinology, 4(6):893–989, 1990).

Omer et al., J. Bacteriol., 172(6):3335–3345, 1990.

Imai et al., PNAS, 86:7823–7827, 1989.

Wen & Fulco, J. Biol. Chem., 262(14):6676–6682, 1989.

Unger et al., J. Biol. Chem., 26193:1158–1163, 1986.

Tobias et al., Science, 254, 1374–1377, 1991.

Schein, Current Opinion in Biotechnology, 2:746–750, 1991.

Gottesman, Methods in Enzymology, 185:119–129, 1990.

Kopetzki et al., Mol. Gen. Genet., 216:149–155, 1989.

Kulisch & Vilker, Biotechnol. Prog., 7:93–98, 1991.

Ohkawa et al., Ann. N.Y. Acad. Sci., 613:37–43, 1990.

Halpert et al., Biochem. Pharmacol., 37(15):3046–3048, 1988.

Zuber et al., PNAS, 85:699–703, 1988.

Megges et al., in Molecular Mechanisms of Adrenal Steroidogenesis and Aspects of Regulation and Application, K. Ruckpaul & H. Rein, Eds., Akademie–Verlag, Berlin, 1990, pp. 204–209.

Richardson & Johnson, Gordon Research Conference on Drug Metabolism, Jul. 15–19 1991, Plymouth, NH.

Dialog Search Report.

Gijutsuin, Kogyo, and Ooeda, Kenji, "Expression Plasmid Aiming at Expression of Rat Heptic Cytochrome P–450MC Gene in *Escherichia Coli*," Patent Abstracts of Japan, 10(144) (C–349)[2201], 1986, JP, A, 615783.

Nebert, D. W. et al., "The P450 Superfamily: Updated Listing of All Genes and Recommended Nomenclature for the Chromosomal Loci," DNA, 8(1):1–13, 1989.

Porter, T. D. et al., "Expression of Mammalian P450s in *Escherichia Coli*," Methods in Enzymology, 206:108–116, 1991.

White, P. C. et al., "Cloning and Expression of cDNA Encoding a Bovine Adrenal Cytochrome P–450 Specific for Steroid 21-Hydroxylation (P–450c21)," Chemical Abstracts, 102(23):160, abstract No. 198924.

Wada, A. et al., "Expression of Functional Bovine Cholesterol Side Chain Cleavage Cytochrome P450 (P450scc) in *Escherichia coli*," Archives of Biochemistry and Biophysics, 290(2):376–380, 1991.

Aoyama, T. et al., "Estradiol Metabolism by Complementary Deoxyribonucleic Acid-Expressed Human Cytochrome P450s," Chemical Abstracts, 113(7):79, abstract No. 52701a, 1990.

Barnes, H. J. et al., "Evaluation of Various Expression Systems for the Synthesis of Cytochrome P–45017a," Journal of Cell Biology, 107(6 part 3):196A, abstract No. 1118, 1988.

Swart, P. et al., "The Catalytic Activity of Human and Bovine Adrenal Cytochromes P45017a," Journal of Cell Biology, 107(6 part 3):196A, abstract No. 1120, 1988.

Barnes, H. J. et al., "Expression and Enzymatic Activity of Recombinant Cytochrome P450 17 α-Hydroxylase in *Escherichia coli*," Proceedings of the National Academy of Sciences of USA, 88:5597–5601, 1991.

Fisher, C. W. et al., "High-Level Expression of Functional Human Cytochrome P450 1A2 in *Escherichia coli*," The FASEB Journal, 6(2):759–764, 1992.

Loman, A. C. et al., "Influence of the Codon Following the AUG Initiation Codon on the Expression of a Modified lacZ Gene in *Escherichia coli*," The EMBO Journal, 6(8):2489∝2492, 1987.

International Search Report for related application, mailed Jul. 10, 1992.

```
        ATG TGG CTG CTC CTG GCT GTC TTT  ...
nat17   Met Trp Leu Leu Leu Ala Val Phe  ...

ATG GCT CTG TTA TTA GCA GTT TTT  ...
mod17   Met Ala Leu Leu Leu Ala Val Phe  ...
```

17αOH >

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 57 base pairs
        ( B ) TYPE: nucleic acid
        ( C ) STRANDEDNESS: unknown
        ( D ) TOPOLOGY: unknown ( i x ) FEATURE:
        ( A ) NAME/KEY: CDS
        ( B ) LOCATION: 1..57

( x i ) SEQUENCE DESCRIPTION: SEQ ID NO:1:

```
ATG GTA GCA AGG GGG CTT CCC CTG CGC TCA GCC CTG GTC AAA GCC TGC     48
Met Val Ala Arg Gly Leu Pro Leu Arg Ser Ala Leu Val Lys Ala Cys
 1           5                  10                 15

CCA CCC ATC                                                         57
Pro Pro Ile
```

( 2 ) INFORMATION FOR SEQ ID NO:2:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Val Ala Arg Gly Leu Pro Leu Arg Ser Ala Leu Val Lys Ala Cys
 1           5                  10                 15
```

Pro Pro Ile (2) INFORMATION FOR SEQ ID NO:3:

(i) SEQUENCE CHARACTERISTICS:
    (A) LENGTH: 57 base pairs
    (B) TYPE: nucleic acid
    (C) STRANDEDNESS: unknown
    (D) TOPOLOGY: unknown (ix) FEATURE:
    (A) NAME/KEY: CDS
    (B) LOCATION: 1..57

(xi) SEQUENCE DESCRIPTION: SEQ ID NO:3:

```
ATG GTC TCC ACA AAG ACC CCT CGC CCC TAC AGT GAG ATC CCC TCC CCT      48
Met Val Ser Thr Lys Thr Pro Arg Pro Tyr Ser Glu Ile Pro Ser Pro
 1               5                  10                  15

GGT GAC AAT                                                          57
Gly Asp Asn
```

(2) INFORMATION FOR SEQ ID NO:4:

(i) SEQUENCE CHARACTERISTICS:
    (A) LENGTH: 19 amino acids
    (B) TYPE: amino acid
    (D) TOPOLOGY: linear (ii) MOLECULE TYPE: protein (xi) SEQUENCE DESCRIPTION: SEQ ID NO:4:

```
Met Val Ser Thr Lys Thr Pro Arg Pro Tyr Ser Glu Ile Pro Ser Pro
 1               5                  10                  15

Gly Asp Asn
```

(2) INFORMATION FOR SEQ ID NO:5:

(i) SEQUENCE CHARACTERISTICS:
    (A) LENGTH: 57 base pairs
    (B) TYPE: nucleic acid
    (C) STRANDEDNESS: unknown
    (D) TOPOLOGY: unknown (ix) FEATURE:
    (A) NAME/KEY: CDS
    (B) LOCATION: 1..57

(xi) SEQUENCE DESCRIPTION: SEQ ID NO:5:

```
ATG GCT CTC ATC CCA GAC TTG GCC ATG GAA ACC TGG CTT CTC CTG GCT      48
Met Ala Leu Ile Pro Asp Leu Ala Met Glu Thr Trp Leu Leu Leu Ala
 1               5                  10                  15

GTC AGC CTG                                                          57
Val Ser Leu
```

(2) INFORMATION FOR SEQ ID NO:6:

(i) SEQUENCE CHARACTERISTICS:
    (A) LENGTH: 19 amino acids
    (B) TYPE: amino acid
    (D) TOPOLOGY: linear (ii) MOLECULE TYPE: protein (xi) SEQUENCE DESCRIPTION: SEQ ID NO:6:

```
Met Ala Leu Ile Pro Asp Leu Ala Met Glu Thr Trp Leu Leu Leu Ala
 1               5                  10                  15

Val Ser Leu
```

(2) INFORMATION FOR SEQ ID NO:7:

( i ) SEQUENCE CHARACTERISTICS:
   ( A ) LENGTH: 57 base pairs
   ( B ) TYPE: nucleic acid
   ( C ) STRANDEDNESS: unknown
   ( D ) TOPOLOGY: unknown ( i x ) FEATURE:
   ( A ) NAME/KEY: CDS
   ( B ) LOCATION: 1..57

( x i ) SEQUENCE DESCRIPTION: SEQ ID NO:7:

```
ATG GCT TTC ATT CCG GAT CTG GCT ATG GAA ACC TGG CTT CTC CTG GCT      48
Met Ala Phe Ile Pro Asp Leu Ala Met Glu Thr Trp Leu Leu Leu Ala
 1           5                  10                  15

GTC AGC CTG                                                          57
Val Ser Leu
```

( 2 ) INFORMATION FOR SEQ ID NO:8:

( i ) SEQUENCE CHARACTERISTICS:
      ( A ) LENGTH: 19 amino acids
      ( B ) TYPE: amino acid
      ( D ) TOPOLOGY: linear ( i i ) MOLECULE TYPE: protein ( x i ) SEQUENCE DESCRIPTION: SEQ ID NO:8:

```
Met Ala Phe Ile Pro Asp Leu Ala Met Glu Thr Trp Leu Leu Leu Ala
 1           5                  10                  15

Val Ser Leu
```

( 2 ) INFORMATION FOR SEQ ID NO:9:

( i ) SEQUENCE CHARACTERISTICS:
      ( A ) LENGTH: 57 base pairs
      ( B ) TYPE: nucleic acid
      ( C ) STRANDEDNESS: unknown
      ( D ) TOPOLOGY: unknown ( i x ) FEATURE:
      ( A ) NAME/KEY: CDS
      ( B ) LOCATION: 1..57

( x i ) SEQUENCE DESCRIPTION: SEQ ID NO:9:

```
ATG GCT TTT ATT CCG GAT CTG GCT ATG GAA ACC TGG CTT CTC CTG GCT      48
Met Ala Phe Ile Pro Asp Leu Ala Met Glu Thr Trp Leu Leu Leu Ala
 1           5                  10                  15

GTC AGC CTG                                                          57
Val Ser Leu
```

( 2 ) INFORMATION FOR SEQ ID NO:10:

( i ) SEQUENCE CHARACTERISTICS:
      ( A ) LENGTH: 19 amino acids
      ( B ) TYPE: amino acid
      ( D ) TOPOLOGY: linear ( i i ) MOLECULE TYPE: protein ( x i ) SEQUENCE DESCRIPTION: SEQ ID NO:10:

```
Met Ala Phe Ile Pro Asp Leu Ala Met Glu Thr Trp Leu Leu Leu Ala
 1           5                  10                  15

Val Ser Leu
```

( 2 ) INFORMATION FOR SEQ ID NO:11:

( i ) SEQUENCE CHARACTERISTICS:
      ( A ) LENGTH: 57 base pairs
      ( B ) TYPE: nucleic acid ( C ) STRANDEDNESS: unknown
( D ) TOPOLOGY: unknown ( i x ) FEATURE:
    ( A ) NAME/KEY: CDS
    ( B ) LOCATION: 1..57

( x i ) SEQUENCE DESCRIPTION: SEQ ID NO:11:

```
ATG GCT CTT ATT CCG GAT CTG GCT ATG GAA ACC TGG CTT CTC CTG GCT      48
Met Ala Leu Ile Pro Asp Leu Ala Met Glu Thr Trp Leu Leu Leu Ala
 1               5                  10                  15

GTC AGC CTG                                                          57
Val Ser Leu
```

( 2 ) INFORMATION FOR SEQ ID NO:12:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met Ala Leu Ile Pro Asp Leu Ala Met Glu Thr Trp Leu Leu Leu Ala
 1               5                  10                  15

Val Ser Leu
```

( 2 ) INFORMATION FOR SEQ ID NO:13:

( i ) SEQUENCE CHARACTERISTICS:
        ( A ) LENGTH: 57 base pairs
        ( B ) TYPE: nucleic acid
        ( C ) STRANDEDNESS: unknown
        ( D ) TOPOLOGY: unknown ( i x ) FEATURE:
        ( A ) NAME/KEY: CDS
        ( B ) LOCATION: 1..57

( x i ) SEQUENCE DESCRIPTION: SEQ ID NO:13:

```
ATG GCT CTC ATT CCG GAT CTG GCT ATG GAA ACC TGG CTT CTC CTG GCT      48
Met Ala Leu Ile Pro Asp Leu Ala Met Glu Thr Trp Leu Leu Leu Ala
 1               5                  10                  15

GTC AGC CTG                                                          57
Val Ser Leu
```

( 2 ) INFORMATION FOR SEQ ID NO:14:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met Ala Leu Ile Pro Asp Leu Ala Met Glu Thr Trp Leu Leu Leu Ala
 1               5                  10                  15

Val Ser Leu
```

( 2 ) INFORMATION FOR SEQ ID NO:15:

( i ) SEQUENCE CHARACTERISTICS:
        ( A ) LENGTH: 57 base pairs
        ( B ) TYPE: nucleic acid
        ( C ) STRANDEDNESS: unknown
        ( D ) TOPOLOGY: unknown ( i x ) FEATURE:

(A) NAME/KEY: CDS
    (B) LOCATION: 1..57

(x i) SEQUENCE DESCRIPTION: SEQ ID NO:15:

ATG GCT CTG TTA TTA GCA GTT TTT CTG GTG CTC CTC TAT CTA TAT GGA    48
Met Ala Leu Leu Leu Ala Val Phe Leu Val Leu Leu Tyr Leu Tyr Gly
 1               5                  10                  15

ACC CAT TCA                                                        57
Thr His Ser (2) INFORMATION FOR SEQ ID NO:16:

(i) SEQUENCE CHARACTERISTICS:
        (A) LENGTH: 19 amino acids
        (B) TYPE: amino acid
        (D) TOPOLOGY: linear (i i) MOLECULE TYPE: protein (x i) SEQUENCE DESCRIPTION: SEQ ID NO:16:

Met Ala Leu Leu Leu Ala Val Phe Leu Val Leu Leu Tyr Leu Tyr Gly
 1               5                  10                  15

Thr His Ser

METHODS AND COMPOSITIONS FOR THE EXPRESSION OF BIOLOGICALLY ACTIVE EUKARYOTIC CYTOCHROME P450S IN BACTERIA

The U.S. government may own certain rights in the present invention pursuant to NIH grant GM37942.

BACKGROUND OF THE INVENTION

1. Field of the Invention

The present invention relates to the functional expression of eukaryotic cytochrome P450s in bacterial cells, genetic constructs for effecting such expression and methods employing these bacteria and/or the recombinant enzyme so produced, e.g., as bioreactors for effecting the metabolism of cytochrome P450 substrates.

2. Description of the Related Art

The cytochrome P450 superfamily includes multiple molecular forms of enzymes which catalyze monooxygenase reactions of a wide variety of endogenous as well as exogenous substrates (Lu, et al., 1980). Each form of these hemoproteins exhibits a unique substrate specificity. The cytochrome P450 superfamily of enzymes participate, for example, in the metabolism of steroids (Hall, 1980), eicosanoid, fatty acids (Kupfer, 1980), and bile acids (Hansson and Wikvall, 1980), as well as exogenous substrates such as drugs, insecticides, and chemical carcinogens (Gelboin, 1980). Comparison of several forms of cytochrome P450 whose primary structures have so far been reported indicates that they are structurally related to one another and possibly derived from a common ancestor (Gotoh, et al, 1983).

Microsomal cytochrome P450s are integral membrane hemoproteins which derive reducing equivalents from NADPH by means of a membrane bound flavoprotein oxido-reductase (NADPH-cytochrome P450 reductase). These so-called mixed-function oxidases activate molecular oxygen so as to insert one atom into a lipophilic substrate and the other atom into water Cytochrome P450 and P450-like enzymes are ubiquitous in nature, being found in a broad range of eukaryotes as well as bacteria. In fact, many of the bacterial enzymes are similar to a certain degree to the P450 enzymes found in mammals. For example, in certain soil bacteria (i.e., *Pseudomonas putida*), the oxygenation of camphor involves an enzyme termed cytochrome P450cAM which acts in concert With an FAD-containing flavoprotein, putida redoxin reductase and an iron sulfur protein putida redoxin (Katagira, et al., 1968) Interestingly, the bacterial electron transfer system in *P. putida* is very similar to the one functional in the mitochondria of higher organisms. However, the electron transfer system of *P. putida* cannot support the functional transfer of electrons to either mitochondrial or microsomal P450s. Because of sequence similarities between the medically important mammalian microsomal P450 (Family IV) and the bacterial fatty acid monooxygenase from *Bacillus megaterium* (cytochrome P450$_{BM3}$), a large amount of effort has been expended in characterizing this and other bacterial enzymes.

While a fair amount of research has been conducted in characterizing bacterial cytochrome P450s, their use in commercial applications, such as in bioreactors, chemical degradation and drug synthesis, has been quite limited. The primary reason for this is that the number of specific forms of bacterial P450s that have been well characterized is very small and the reactions that these enzymes catalyze are of limited biomedical or commercial value. In contrast, a vast number of eukaryotic and mammalian P450s have been characterized. More importantly, these enzymes catalyze reactions involved in drug, steroid and xenobiotic metabolism all of which have a direct impact on human health. This is unfortunate in that bacterial expression systems offer many advantages over expression in yeast and mammalian cells in that bacterial systems may be used to produce proteins in large quantities, at low cost, with unparalleled ease.

In contrast to the disadvantages associated with the use of bacterial cytochrome P450s, the eukaryotic enzymes offer many advantages, including metabolism of drugs and other molecules of importance to human health. Unfortunately, present eukaryotic systems for the production of eukaryotic cytochrome P450s are hampered by several serious drawbacks including low rates of production, the use of expensive tissue culture materials and facilities as well as the requirement for sophisticated methodologies, and extensive destruction of the enzyme by the expression host or even lack of biological activity.

Accordingly, there is a great need for the development of technology which would combine the advantages of bacterial expression with those of eukaryotic and mammalian cytochrome P450s. Although bacteria have demonstrated great utility in the expression of many prokaryotic and eukaryotic proteins, bacterial expression systems for cytochrome P450 have heretofore been limited to the soluble bacterial forms of this gene superfamily (Unger, et al., 1986). Although yeast (Oeda, et al., 1985), COS 1 (Zuber, et al., 1986) and virally infected eukaryotic cells (Battula, et al., 1987; Asseffa, et al., 1989) have been used as hosts for the heterologous expression of P450 molecules, each has limitations to their usefulness as expression systems. Unfortunately, the present understanding in the art is that eukaryotic cytochrome P450s simply cannot be expressed functionally in bacteria (Collin, et al., 1988).

Due to the existence of numerous disadvantages with current systems for the expression of biologically active cytochrome P450s, there exists a continuing need for the development of novel systems, particularly bacterial expression systems, which can be used to produce biologically active cytochrome P450 enzymes. There is a particular need for bacterial expression systems for expressing biologically active eukaryotic cytochrome P450s which incorporate the advantages of bacterial expression. The development of novel technology which addresses one or more of these disadvantages would have broad research and commercial applications including steroid and prostaglandin biosynthesis, as bioreactors, in drug development and characterization, and even environmental clean up.

SUMMARY OF THE INVENTION

The present invention addresses various of the foregoing and other disadvantages in the art by providing for the first time methods and compositions for the expression of biologically active eukaryotic cytochrome P450s in bacterial systems. Therefore, in general, the present invention concerns stably transformed bacterial cells which express a biologically active eukaryotic cytochrome P450 enzyme, methods for the production of biologically active cytochrome P450 enzymes in recombinant bacteria, methods for the metabolism of cytochrome P450 substrates in such bacteria, DNA segments encoding eukaryotic cytochrome P450 enzymes which have been modified to allow effective bacterial expression, as well as methods for obtaining bacterial expression of a biologically active eukaryotic cytochrome P450 enzyme.

Accordingly, in certain embodiments, the invention concerns stably transformed bacterial cells which express a biologically active eukaryotic cytochrome P450 enzyme. The eukaryotic P450 is encoded by a recombinant cytochrome P450 gene, having associated expression elements capable of effecting bacterial transcription and translation of the P450 gene. These elements include a bacterially compatible ribosome binding site, spacer region, transcription terminator, and promoter elements. As used herein, the term "bacterially compatible" is intended to refer to genetic elements that are compatible with and therefore capable of functioning in bacteria and include generally bacterial elements, phage elements and the like.

The development of the present invention rests in part on the inventor's discovery that most, if not all, eukaryotic P450 genes must be structurally modified so as to allow their expression in bacteria in a biologically active form. Most generally, this will include combining the eukaryotic cytochrome P450 gene with bacterial expression elements such as a bacterially compatible ribosome binding site, spacer region, transcription terminator and promoter. This is because most corresponding eukaryotic elements will not adequately function in bacterial hosts. One will typically desire in connection with most if not all eukaryotic cytochrome P450s, to modify the eukaryotic structural gene to effect an improved bacterial expression capability. Modification of the codon for the second amino acid may be necessary to effectuate biologically active bacterial expression (where the second codon is defined as that codon which immediately follows the translation start codon, ATG).

It is proposed that it may be necessary to modify the codon encoding the second amino acid of the eukaryotic cytochrome P450 enzyme to reflect a codon preferred for bacterial expression. The preferred codons include GCT (Ala), AAA (Lys), ACC, ACT (Thr), TAT (Tyr), AAT, AAC (Asn), CAC, CAT (His), CGT, AGA, CGC (Arg), TTT (Phe), ATC, ATA, ATT (Ile), GTA (Val), TTG, CTT, CTC, TTA (Leu), GCC, GCA (Ala), GAA (Glu), AGC, and AGT (Ser). Of these, GCT and AAA will be particularly preferred. Note that certain second codons should be avoided for bacterial expression, including TTC (Phe), CTA, CTG (Leu), TCA, TCT, TCC, TCA, TCG (Ser), CCG, CCT, CCC, CCA (Pro), ACA, ACG (Thr), GCG (Ala), CAG, CAA (Gln), GAT, GAC (Asp), GAG (Glu), TGT, TGC (Cys), TGG (Trp), CGG, AGG (Arg), GGT, GGC, GGA, GGG (Gly), ATG (Met), GTT, GTC, GTG (Val), TAC (Tyr), and AAG (Lys).

An additional or alternative modification which the inventor has found to provide benefits in accordance with the invention includes ensuring that the codon encoding the fourth and/or fifth amino acid of the eukaryotic cytochrome P450 (as measured from the start codon) comprises an AT rich codon. As used herein, the phrase "AT rich" codon is intended to refer to a codon which includes at least two As or Ts and preferably all three nucleotides of the codon should be an A or a T. Of course, where possible, one will desire to leave the same amino acid encoded at the fourth and fifth position and yet select a codon for this amino acid that is AT rich. Thus, for example, where the fourth and fifth amino acids are Leu and encoded by CTC or CTG, one can modify these positions to incorporate and AT rich codon such as TTA and achieve the objective of an AT rich codon without changing the encoded amino acid.

In other embodiments, advantages in accordance with the invention may be realized by ensuring that the first 25 codons of the cytochrome P450 gene includes not more than 2 rare codons. As used herein, the term "rare codon" is intended to refer to those codons which are used at a frequency of less than 10% for the amino acid which they encode, and include CTA, TCA, AGT, ACA, GGA, CCC, ATA, GGG, CGA, CGG, AGA, AGG. More preferably, one may desire to ensure that the first 25 codons of the eukaryotic cytochrome P450 gene are devoid of rare codons, particularly AGA (Arg) and AGG (Arg).

An additional modification which may prove beneficial is the alteration of the coding sequence in a manner which will act to disrupt possible unfavorable secondary mRNA structure within approximately 20 nucleotides 5' or 3' of the ATG initiation codon. It is believed that the translational efficiency of bacterial mRNAs is dependent on the degree to which this region of single stranded RNA is unfolded. The greater the degree of an extended, open conformation in this region, as opposed to a folded structure stabilized by intramolecular base pairing, the greater the translational efficiency and subsequent synthesis of the gene product. Therefore, it may be helpful to alter specific nucleotides in this region to disrupt potential secondary structure. Several mathematical algorithms are available in software packages to predict the structure and stability of RNA's (see, e.g., Jaeger et al., 1989). These programs may be used to predict the stability of alternative mRNA sequences. Judicious changes in nucleotide sequence can significantly reduce the stability of secondary structures and therefore provide a better template for transcription initiation.

While the introduction of the foregoing modifications into eukaryotic cytochrome P450s may prove to be necessary in many instances, the inventor contemplates that these modifications will not always be required in that some eukaryotic cytochrome P450s may be expressed directly. In these instances, however, it will nonetheless be necessary to combine the cytochrome P450 with appropriate elements which are capable of effecting bacterial transcription and translation, including a bacterially compatible ribosome binding site, spacer region, transcription terminator, and promoter.

In terms of the promoter, it is believed that virtually any promoter functional in the selected bacterial host may be employed. However, preferred promoters include the tac, lac, lac UV5, tac, trc, $\lambda P_L$, T7 or T3 promoter. Of course, the $\lambda P_L$, T7 and T3 promoters are derived from baoteriophage and are known to be functional in bacteria such as E. coli. While conventional wisdom would suggest that strong promoters would be preferred, the present inventor has observed that this may not be the case for the functional expression of eukaryotic cytochrome P450s in bacteria. For example, while the T7 gene 10 promoter is one of the strongest promoters yet identified, its use in connection with the cytochrome P450 17α-hydroxylase ($P_{450}17\alpha$) results in the expression in E. coli of large amounts of the enzyme, much of which, however, is spectrally inactive and found in an insoluble form. Similar results are found with the use of a lac promoter, another strong promoter. It is possible that subtle changes in growth media, temperature and or induction regimen may be necessary for functional expression in these systems. Of particular interest is the possibility that hemin (a cofactor of all functional p450 enzymes) may be limited in these cells. Thus, the addition of exogenous hemin may be necessary to effect functional expression in these systems.

The inventor has found that the preferred promoter for bacterial expression is the tac promoter/ribosome binding site, which is available in "cassette" form (Pharmacia 27-4883-01). The activity of this promoter is negatively regulated by the production of the lac repressor from a cloned copy of the lac I gene.

One will often desire to incorporate into the eukaryotic cytochrome P450 gene an appropriate ribosome binding site for effectuating bacterial expression. Often, the ribosome binding site and promoter can be incorporated as a "cassette", defined as a contiguous, pre-fabricated DNA segment which incorporates the desired elements and has useful restriction enzyme recognition sites at its two termini, allowing it to be readily inserted at an appropriate point within the desired cytochrome P450 gene by simple genetic manipulation.

Most conveniently, one may desire to simply employ a promoter and ribosome binding site from a homologous system, such as the T7 promoter and its associated ribosome binding site (RBS), or the lac promoter and its associated RBS. In general, however, it is proposed that one may employ any effective bacterial ribosome binding site, with those RBSs from $E.\ coli$, $\lambda$, T7 or T3 being preferred. Even more preferred ribosome binding sites are those from the T7 gene 10, or $E.\ coli$ lac a, lac z, trp A, trp B, trp C, trp D, trp E, trp L, trp R or trp S genes. A particularly preferred ribosome binding site and spacer region comprises the sequence 5'-AGGAGGT-CAT-3', wherein the underlined portion comprises the ribosome binding site and the adjacent CAT sequence comprises the spacer region. (The spacer region is that sequence between the ribosome site and the ATG initiation codon.)

One will also typically desire to incorporate into the eukaryotic cytochrome P450 gene an appropriate bacterial transcription terminator, which functions to terminate the function of bacterial RNA polymerases, the enzymes responsible for transcribing DNA into RNA. The requirements for a functional bacterial transcription terminator are rather simple, and are usually characterized by a run of T residues preceded by a GC rich dyad symmetrical region. The more preferred terminators are those from the TRP gene, the ribosomal terminators, rrnB, or terminator sequences from the T7 phage. In fact, the T7 terminator sequences contain RNase III cleavage sites with a stem-loop structure at the 3' ends of mRNAs which apparently slows down message degradation.

While the present invention is exemplified through use of a 17α-hydroxylase P450 gene, it is believed that the techniques disclosed herein will be generally applicable to all eukaryotic cytochrome P450s, many of which have similar structural and functional characteristics. Thus, it is proposed that the invention will be generally applicable to members of the cytochrome P450 I, II, III, IV, VI, XIA, XIB, XVII, XIX, XXI and XXVI family. However, for commercial applications it is proposed that preferred cytochrome P450 for application in connection with the present invention will be the steroid hydroxylases, steroid biosynthetic enzymes P450 XIA1 (SCC), P450 XIB1 (11β), P450 XVIIA1 (17α), P450 XIXA1 (aromatase) and P450 XXI (C21) and the xenobiotic metabolizing enzymes P450 I ($P_1$ and $P_3$), P450 II (1, LM2, mp, db1, and j), P450 III (nf) and P450 IV (LA).

Moreover, although the present invention is exemplified in terms of an $E.\ coli$ bacterial host, there is no reason why other types of bacteria cannot be employed in place of $E.\ coli$. For example, one may desire to employ a member of the gram negative family Enterobacteriaceae, which comprise 18 genera. The most closely related to $E.\ coli$ are Salmonella and Shigella, and less closely related are the Enterobacter, Serratia, Proteus and Erwinia. Of these, expression of P450 in Salmonella, Bacillus and Pseudomonas, may be preferred.

A particularly surprising aspect of the present invention is the finding that recombinant bacteria have been found to produce a biologically active eukaryotic cytochrome P450 enzyme without the need for an associated eukaryotic cytochrome P450 reductase. Although cytochrome P450 enzymes require the presence of a reductase or associated electron transfer capability in order to function, it is apparently the case that the bacterial system set forth herein produce an electron transfer capability that is capable of substituting for eukaryotic P450 reductases. However, for certain applications it may be necessary to cotransform bacteria with an appropriate eukaryotic or prokaryotic P450 reductase expression plasmid in order to achieve a maximally active enzyme. The inventor proposes that this reductase may most preferably be introduced on a plasmid together with the selected P450 enzyme gene or on a separate plasmid under a different antibiotic selection than the recombinant P450. Alternatively, the cDNA encoding the reductase may be integrated into the $E.\ coli$ genome to produce a bacterial cell line which synthesizes this auxiliary enzyme. Additionally, the reductase need not be of eukaryotic origin as the reductase moiety of cytochrome P450 BM3 (of Bacillus magaterium) has been shown to be capable of electron transfer to eukaryotic P450s.

As noted, the present invention also concerns methods for the production of the biologically active eukaryotic cytochrome P450 enzyme in a recombinant bacterium which includes preparing a bacterial cell as discussed above and culturing the cell under conditions appropriate to effectuate expression of the cytochrome P450 enzyme in a biologically active form.

In still further embodiments, the invention concerns a method for the metabolism of a cytochrome P450 substrate which includes preparing a bacterial cell which expresses a biologically active cytochrome P450 enzyme as discussed above, wherein the expressed enzyme is selected to be capable of metabolizing the substrate, and subjecting the substrate so produced under conditions which will allow the substrate to be metabolized. Of course, the cytochrome P450 enzyme gene is selected such that the encoded enzyme will function to metabolize the particular substrate. While one may desire to at least partially purify the enzyme from the bacterium prior to subjecting the substrate to the enzyme, it is proposed that one may simply employ the recombinant bacteria directly, in that P450 substrates are typically hydrophobic compounds and would be expected to diffuse across biological membranes of intact bacteria to encounter the enzyme. Alternatively, one may desire to first partially purify the enzyme, for example, by simply isolating bacterial membrane fractions which include the enzyme. This is achieved most readily by breakage of the recombinant bacteria by enzymatic, mechanical or sonic disruption and then isolating the bacterial membranes via differential centrifugation.

In still further embodiments, the invention concerns a method for obtaining bacterial expression of a biologically active eukaryotic cytochrome P450 enzyme. This includes first obtaining a DNA segment which comprises a selected eukaryotic cytochrome P450 enzyme gene, and modifying the segment so as to operatively combine the gene with the bacterially compatible ribosome binding site, spacer region, transcription terminator and promoter to form a bacterial expression unit. Next, bacteria are transformed with the bacterial expression unit to form transformant colonies. Then a transformant colony which expresses the gene in a biologically active fashion is selected and cultured under conditions to effect expression of the eukaryotic cytochrome P450 enzyme. The inventor proposes that a particularly advantageous method for achieving expression is to form the promoter, ribosome binding site, spacer region, as well as the various genetic modifications discussed above for effecting improved bacterial expression, into a single bacterial expression plasmid which can be universally employed with any of the eukaryotic cytochrome P450 genes. It is envisioned that such a plasmid will be universally applicable and will comprise the bacterial control elements in combination with the first 10 or so codons modified for bacterial expression, followed by restriction enzyme site(s) which will allow one to splice this amino terminal coding region into the cDNA of the P450 one wishes to express. Using standard techniques one of these restriction sites will be introduced into the P450 cDNA at or near the 10th codon. One may then clone this cDNA into the expression plasmid such that the elements necessary for efficient bacterial expression (i.e. promoters, rbs, spacer region and the modified amino terminal codons) are placed in front of the P450 cDNA. Thus, a hybrid P450 is created in which the native 5' codons of any eukaryotic P450 are effectively replaced by modified codons which have a demonstrated ability to promote bacterial expression.

BRIEF DESCRIPTION OF THE DRAWINGS

FIG. 2(A) shows the nucleotide changes (indicated in bold letters) that were introduced through the use of PCR mutagenesis of plasmid pCD17α-2.

DETAILED DESCRIPTION OF PREFERRED EMBODIMENTS

Figure 1:
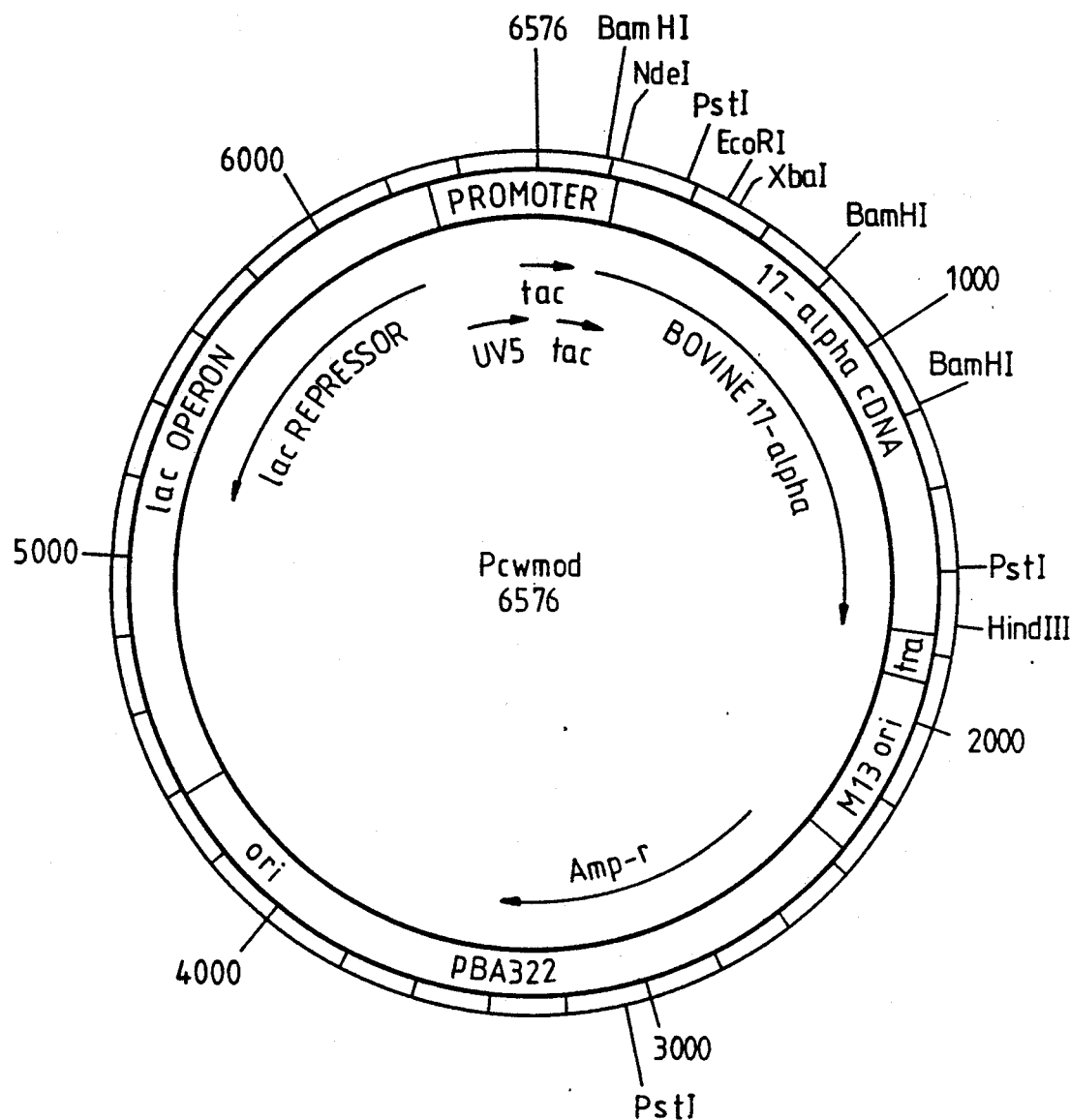
FIG. 1 Restriction map of the pCWmod17 plasmid employed in the preparation of recombinant bacteria which express $P450_{17\alpha}$ (ATCC accession number 68511, deposited Jan. 9, 1991.

The present inventor has developed a bacterial expression system for producing mammalian cytochrome P450s in an enzymatically active form. Generally speaking, this has been achieved through the modification of a eukaryotic cytochrome P450 gene to incorporate bacterial expression elements including a bacterially compatible ribosome binding site, spacer region, transcription terminator and promotor. Additionally, as discussed in general terms above, the inventor has determined that one may find it necessary to modify the coding sequence of the eukaryotic P450 gene to render the amino terminal coding region acceptable for bacterial expression.

While the present invention is exemplified through the use of a cDNA gene for bovine 17α-hydroxylase ($P450_{17\alpha}$), it is proposed that the techniques and modifications disclosed herein will be applicable to eukaryotic cytochrome P450s in general. Furthermore, although the invention is exemplified through the use of an $E.$ $coli$ host, it is proposed that the invention will be generally applicable to other bacterial hosts, particularly those related to $E.$ $coli,$ and their uses not excluded. Surprisingly, it has been found that the bacterial host used to exemplify the invention contains an electron transport system that can substitute for the mammalian microsomal NADPH-cytochrome 450 reductase in supporting the 17α-hydroxylase and 17, 20-lyase activities of $P450_{17\alpha}.$ Thus, it is proposed that one may often be able to employ such hosts without the need for adding extrinsic reductase or incorporating a separate mammalian reductase gene into the bacterial host.

An important aspect of the present invention is the use of a bacterial ribosome binding site, spacer region and terminator. Suitable elements in this regard are well known in the art and they may be combined with the selected cytochrome P450 gene in appropriate fashion through the application of well known techniques.

Although there are hundreds of $E.$ $coli$ promoter sequences, only a handful of these are typically employed in bacterial expression systems. These tend to be strong promoters that are highly regulated. The most commonly employed, and those generally preferred for use in the present invention, are the trp, lac (or hybrids of these such as the lac UV5 tac and trc promoters), $\lambda P_L$, as well as promoters found in the genes of other $E.$ $coli$ Viruses such as T7 or T3. The tac promoter has proved to be particularly beneficial. If one does not desire to employ the tac promoter, it is believed that other promoters may be substituted, with the lacZ, T7 and $\lambda P_L$ being preferred. However, the present invention is by no means limited to these embodiments and one may refer to publications such as Hawley et al., 1983, and Hoopes et al., 1987 for other useful promoters.

Although the conventional wisdom is that strong promoters are the best promoters, the inventor's studies have indicated that this may not hold true for the functional expression of a eukaryotic cytochrome P450 such as P450$_{17\alpha}$. The reason for this is that when the modified 17α cDNA is placed into an expression vector containing a promoter, ribosome binding site and spacer region of gene 10 from T7 virus, it was expressed in *E. coli* in large amounts but most of the protein was spectrally inactive and found in a relatively insoluble form in the cells. Interestingly, the T7 promoter is one of the strongest promoters yet identified and the RBS and spacer region are most certainly very efficient in translation initiation and elongation. However, similar results are observed with a clone containing a lac promoter along with the RBS and spacer region of gene 10 upstream of the modified cDNA 17α sequence. While the reason for this is unclear, the inventor's working hypothesis in this regard is that eukaryotic P450s need to be synthesized slowly in a highly regulated manner such that the cells are given time to metabolically adapt to the production of this foreign protein.

The use of a bacterially compatible ribosome binding site also appears to play an important role in the practice of this invention. Generally speaking, it is believed that most known ribosome binding sites, and their associated spacer regions, may be employed to some advantage in connection with this invention. Numerous such RBS are known (Gren, 1984). The Gren article, in fact, discloses a large number of ribosome binding sites and their associated spacer regions which have been sequenced from RNA phage, DNA phage and *E. coli* μgenes. While it is believed that virtually any of these ribosome binding sites may find utility in connection with the present invention, it is believed that the particularly preferred ribosome binding sites will be those from DNA phage, the T7 phage, as well as various *E. coli* genes. Of these, those that are particularly preferred are the RBS and spacer from the T7 gene 10, *E. coli* lac a, lac z, trp A, trp B, trp C, trp D, trp E, trp L, trp R, and trp S. For the optimization of RBS structure, one may wish to refer to DeBoer et al., 1990.

The upstream region of the inventor's most preferred embodiment, the pCW plasmid (discussed in more detail below), is 5'-ATCGATGCTTAGGAGGTCATATG-3', wherein the first underlined portion is the RBS and the second is the initiation codon (ATG). The rbs here is seven nucleotides and is combined with a rather short spacer of three nucleotides (CAT). Thus, the RBS is longer than necessary while the spacer is suboptimally short, at least this is what one would expect based on what is known about most RBS/spacer combinations.

The use of a bacterial transcription terminator is also an important aspect of the invention. In general, it is believed that one may employ virtually any bacterial terminator sequence. A useful listing of terminator sequences which the inventor believes one may use in connection with the present invention can be found in Rosenberg et al., 1979. Generally speaking, simple bacterial terminators are characterized by a series of thymidine residues at the 3' end of the gene, preceded by a GC-rich region of dyad symmetry in the DNA. Some terminators have a run of adenines (preceding the GC-rich region) that can apparently provide a symmetric counterpart to the uridine-encoding region, and should thus function in both directions. This has been demonstrated for rho indepedant terminators and for the rrnB operon.

Terminators seem to be important in the stability of plasmids carrying strong promoters. The terminators which are most frequently used in expression vectors are the trp or the ribosomal terminators, rrnB. Terminator sequences from T7 phage have also been used frequently in expression vectors since they contain RNase III cleavage sites which leave a stem-loop structure at the 3' ends of mRNAs that apparently slows down the degradation of these messages in *E. coli* (Danayotatos et al., 1985).

An important aspect of the invention concerns the modification of the eukaryotic cytochrome P450 enzyme gene to insure a nucleotide sequence that favors expression in a bacterial host. A principal focus of these modifications is the codon which codes for the second amino acid of the enzyme, measured from the initiation codon, ATG. Studies undertaken by others have demonstrated that the second codon can influence the expression efficiency of the lac Z structural gene, and found that certain codons are preferred over others where an enhanced efficiency is desired (see Looman et al., 1987). Surprisingly, the present inventor has found that the second codon, at least in the context of eukaryotic cytochrome P450 expression, plays a role in the generation of biologically active eukaryotic P450 enzymes as well. For example, when the second codon of P450$_{17\alpha}$ is modified to incorporate a codon highly preferred for bacterial expression, in combination with additional modifications discussed below, a biologically active enzyme is produced. However, when the second codon of P450$_{17\alpha}$ is left unchanged in its natural state (TGG), and additional modifications are not made, no detectable biologically active enzyme is produced.

The inventor proposes that one will desire to modify the second codon of a selected cytochrome P450 enzyme gene so as to incorporate a codon preferred for bacterial expression. Exemplary preferred codons include GCT (Ala), AAA (Lys), ACC, ACT (Thr), TAT (Tyr), AAT, AAC (Asn), CAC, CAT (His), CGT, AGA, CGC (Arg), TTT (Phe), ATC, ATA, ATT (Ile), GTA (Val), TTG, CTT, CTC, TTA (Leu), GCC, GCA (Ala), GAA (Glu), AGC, AGT (Ser). Of these, the GCT codon is particularly preferred. Of course, where possible, one will desire to modify the second codon so as to maintain the same primary amino acid structure of the resultant expressed enzyme. This will be possible, however, only where the second amino acid is Phe, Leu, Ile, Val, Thr, Ala, Arg, Asn, Glu, His, Lys, Ser, or Tyr, in that no preferred codons exist for the remaining amino acids (Met, Pro, Gln, Asp, Cys, Gly, Trp).

Just as some codons are to be preferred at the second position, certain codons are to be avoided. For example, the inventor has prepared a construct which comprised the native P450$_{17\alpha}$ sequence, except that the second codon was changed, to GGG (Gly), placed downstream from the strong trc promoter. This construct failed to produce any immunodetectable protein. Thus, GGG is to be avoided. It is believed that other codons which should be avoided include TTC (Phe), CTA, CTG (Leu), TCA, TCT, TCC, TCA, TCG (Ser), CCG, CCT, CCC, CCA (Pro), ACA, ACG (Thr), GCG (Ala), CAG, CAA (Gln), GAT, GAC (Asp), GAG (Glu), TGT, TGC (Cys), TGG (Trp), CGG, AGG (Arg), GGT, GGC, GGA, GGG (Gly), ATG (Met), GTT, GTC, GTG (Val), TAC (Tyr), and AAG (Lys).

A second consideration which appears to be important in the modification of P450 genes to effect biologically active bacterial expression is the nucleotide sequence between nucleotides 10 and 15 (i.e., codons 4 and 5). It has been proposed by Stormo, et al. 1982 that it is important to maintain an AT richness in this region where one desires to promote bacterial expression. Thus, in modifying eukaryotic P450 enzymes for bacterial expression, one will desire to introduce codons which have at least two A or T residues, and preferably three such residues. These modifications will preferably result in "silent" mutations which will not change the resultant amino acid structure of the enzyme. Of course, certain amino acids are encoded only by codons which, at most, have only one A or T residue (e.g., Gly, Ala, or Pro). Where the fourth or fifth amino acid of the selected P450 enzyme is one of these, it may be necessary to modify the primary amino acid sequence in order to introduce an appropriate codon sequence at these positions.

An additional modification which may prove beneficial is the introduction of homology sequences which will promote transcription initiation and or elongation in $E.\ coli$. These considerations are based on the finding by Peterson et al., 1988, that the vast majority of $E.\ coli$ mRNAs (greater than 98%) contain at least three consecutive nucleotides from the sequence 5' TCAAACTCTTCAATTT 3' within the first 21 nucleotides following the ATG initiation codon. It will be noted that the modified codons of P450$_{17\alpha}$ described herein contain several of these nucleotides in the prescribed location. Namely, the sequence CTCT is found within codons two (GCT) and three (CTG) while the triplet TTT is found reiterated in codons seven and eight (GTT TTT). Such sequences are thought to be involved in base pairing with the 5' terminus of bacterial 15S ribosomal RNA, which is an important step in efficient transcription initiation and or elongation in $E.\ coli$. Such sequences are preferably introduced into eukaryotic P450 cDNA sequences if they do not already contain them.

Additionally, it is proposed that the presence of rare codons, especially AGA and AGG coding for Arg, within the first 25 codons will be deleterious to efficient expression (Chen et al., 1990). Additional rare codons which one might seek to avoid include CTA, TCA, AGT, ACA, GGA, CCC, ATA, GGG, CGA, CGG, AGA, and AGG.

Another matter of potential focus concerns the second amino acid. Others have found that the size of the side chain of the second amino acid determines whether the N-terminal Met residue will be removed (Hirtel et al., 1989; Dalobge et al., 1990). This becomes important in light of studies by Bachmair et al., 1988, which demonstrate that the N-terminal amino acid of a protein determines its rate of degradation in the cell. If the native second amino acid leads to N-terminal Met processing and the next exposed amino acid gives rise to a protein with a short half-life, one will desire to alter this residue to prevent such an occurrence. Thus, one may consider ensuring that the second amino acid is Ser, Ala, Thr, or Val.

It is proposed that virtually any bacterial expression vector which is adapted for the particular bacterial host that is selected can be employed in the practice of the present invention. Of course, it may be necessary to modify the expression vector to take into account the considerations discussed above in terms of not only the appropriate ribosomal binding site, spacer region and effective promoter, but also the various modifications for effecting improved bacterial expression. Nevertheless, it is proposed that virtually any appropriate bacterial expression plasmid may be employed where desired, at least as a starting point. These may include but are not limited to pBR322, pASI, pUC7-19, pKK (223-3, 233-2, 177-3, 240-11), pTrc99A-C, pDR540, pDR720, pPL-lambda, pKC30, pSK(+/−), Pin-iii, pCZ198, pTTQ8,9,18,19 and 181, pGEMEX-1 and 2, pET1-5, pT7-3-7 and the like.

A preferred plasmid for use in connection with the present invention is designated pCW, which has a restriction map as shown in FIG. 1. The pCW plasmid which was employed in connection with certain aspects of this invention is a derivative of the plasmid disclosed in Muchmore et al., 1989. Synthesis of cloned cDNAs is driven from two copies of a tac promoter/ribosome binding site cassette (Pharmacia 27-4883-01). The activity of this promoter is negatively regulated by the production of the lac repressor from a cloned copy of the lac I gene present in this plasmid. (The pCW vector has very tight regulation of expression, since this vector contains the lac I$^q$ gene, which may be an important factor for expressing eukaryotic P450s in $E.\ coli$). Upon addition of IPTG to the cells, repression s relieved and synthesis proceeds from the tac promoters through the inserted cDNA and stops at a downstream transcription terminator.

While information provided to the inventor by the developer of this plasmid indicated that the DNA sequence between the last tac promoter and the ATG codon of the cloned DNA (i.e., the "spacer region") is derived from the T4 lysozyme gene, a preliminary search of the lysozyme gene failed to uncover the presence of this sequence. Furthermore, this spacer also contains an ATG codon which may also initiate protein synthesis due to its proximity to ribosome binding sites in the tac promoter cassette. Therefore, in that the precise structure of this clone is not clear, the inventor has deposited samples of the clone which contain the modified P450$_{17\alpha}$ gene discussed in the examples below with the ATCC on Jan. 9, 1991, as deposit number 68511, deposited Jan. 9, 1991, under the provisions of the Budapest Treaty.

In order to use this plasmid for the expression of other P450 genes, an Nde 1 (CATATG) restriction enzyme site is preferably introduced at the ATG initiation codon of the P450 cDNA in question if one does not naturally occur there. In addition, other sequence alterations (described in detail herein) may also need to be introduced into the 5'-coding sequence of the P450 cDNA. A unique restriction enzyme cloning site downstream of the P450 coding sequence is preferably employed to clone the P450 DNA fragment into the plasmid expression vector. A Hind III site (AAGCTT) is preferred since this is the site found in the present plasmid. (However, other unique restriciton sites may be rendered compatible to this Hind III site through standard molecular biology techniques). These alterations are most easily accomplished by the synthesis of oligonucleotides containing the desired sequence changes and the subsequent introduction of these mutations into the P450 gene by standard PCR mutagenesis techniques (Higuchi et al., 1988). To introduce the alternative P450 coding sequence into the expression vector, the plasmid DNA would thus be digested with the appropriate enzymes, in this case Nde 1 and Hind III. The vector DNA fragment is isolated from the P450$_{17\alpha}$ insert fragment and mixed with the approximately digested alternative P450 cDNA sequence in the presence of T4 DNA ligase. The vector now carrying the alternative P450 cDNA sequence is introduced into *E. coli* by standard techniques and used to produce the P450 enzyme according to the methods described herein.

Of course, where bacteria other than *E. coli* are employed, one will desire to use a plasmid that is specifically adapted for use in the selected host. Representative shuttle vectors that replicate in *E. coli* and *B. subtilis* are the pHV series plasmids and derivatives of pVB110. Representatives of tretomyces plasmids are the high copy number plasmids pIJ, pFJ and their derivatives. While the present invention is exemplified in terms of an *E. coli* host, it is believed that virtually any bacterial host that is amenable to cloning an expression of foreign genes may be employed in connection with this invention. A number of exemplary hosts other than *E. coli* are known in the art to be useful for this purpose and include Bacillus, Streptomyces, and Pseudomonas. The inventor proposes that one will desire to employ a member of the gram negative family Enterobacteriaceae, which is the family of which *E. coli* is a member. It is proposed that many members of the other 18 μgenera of the family Enterobacteriaceae will be suitable expression host. The most closely related *E. coli* are Salmonella and Shigglia, which are also found in the intestinal tracts of vertebrates.

Enterobacter, Serratia, Proteus and Erwinia are less closely related genera. Of all these bacteria, expression of P450 in Salmonella may have commercial value since this is the host organism for the Ames test which is used to evaluate the carcinogenic activity of chemicals. Expression of drug metabolizing P450s in Salmonella could allow for carcinogen activation in vivo as opposed to preincubation of the chemical with a liver extract which is presently necessary to detect compounds which must first be metabolized before they become mutagenic. Other bacteria that might express eukaryotic P450s are those which synthesize bacterial forms of these enzymes. P450s have been identified in Bacillus and Pseudomonas. These are by no means the only bacteria which contain P450 but rather the only ones in which P450s have been well characterized.

One should also consider the fact that eukaryotic P450s are not self sufficient enzymes in that they require oxygen and a reductase enzyme which transfers electrons from NADPH to the P450. Thus, potential expression hosts can not be anaerobes but must be aerobes or facultative anaerobes. The bacteria must be able to grow in the presence of $O_2$. Secondly, the host organism must have a protein capable of transferring electrons to the P450 enzyme. From the inventor's data it appears that *E. coli* contains such a protein. One might reasonably conclude that other bacteria (especially those bacteria closely related to *E. coli*) also contain an identical or similar protein. Even if a given bacteria lacks such a reductase it is possible to coexpress this protein along with the desired P450.

With the foregoing considerations in mind, the inventor proposes that the present invention will be generally applicable to all eukaryotic cytochrome P450s. A large number of eukaryotic cytochrome P450s have been cloned and their cDNA sequences published and therefore generally available to the art. The following table, Table 1, was generated from the article of Nebert et al., 1989, and sets forth all of the known P450 families, representative members of each family, and references which describe the particular P450 genes. One may wish to refer to the original Nebert et al. publication for the particular reference citations, which has been left off of the Table 1 which follows. It will be appreciated that Table 1 also includes many of the known bacterial P450s, including those from *C. tropicalis, Ps. putiva,* and *B. megaterium*.

TABLE 1

| P450 Genes and Their Products | | | | | | |
|---|---|---|---|---|---|---|
| Family | Locus Symbol | Protein Name | Trivial Name | Species and Source[a] | | References |
| 1 | CYP1A1 | IA1 | c | Rat | D | Sogawa et al. (1984) |
| | | | | | R | Yabusaki et al. (1984) |
| | | | | | D | Hines et al. (1985) |
| | | | $P_1$ | Mouse | R | Kimura, S. et al. (1984b) |
| | | | | | R | Kimura, S. et al. (1987b) |
| | | | $P_1$ | Human | R | Jaiswal et al. (1985a) |
| | | | | | D | Jaiswal et al. (1985b) |
| | | | | | R | Quattrochi et al. (1985) |
| | | | | | D | Kawajiri et al. (1986) |
| | | | form 6 | Rabbit | R | Okino et al. (1985) |
| | | | | | R | Kagawa et al. (1987) |
| | | | IA1 | Trout | RD | Heilmann et al. (1988) |
| | CYP1A2 | IA2 | d | Rat | R | Kawajiri et al. (1984) |
| | | | | | D | Sogawa et al. (1985) |
| | | | | | P | Haniu et al. (1986) |
| | | | $P_3$ | Mouse | R | Kimura, S. et al. (1984a) |
| | | | | | R | Kimura, S. et al. (1984b) |
| | | | $P_2$ | Mouse | R | Kimura and Nebert (1986) |
| | | | $P_3$ | Human | R | Jaiswal et al. (1986) |
| | | | | | R | Jaiswal et al. (1987) |
| | | | form 4 | Human | R | Quattrochi et al. (1985) |
| | | | | | RD | Quattrochi et al. (1986) |
| | | | LM4 | Rabbit | P | Fujita et al. (1984) |
| | | | | | R | Okino et al. (1985) |
| | | | | | P | Ozols (1986) |
| | | | | | R | Kagawa et al. (1987) |
| IIA | CYP2A1 | IIA1 | a1 | Rat | R | Nagata et al. (1987) |
| | CYP2A2 | IIA2 | a2 | Rat | R | Matsunaga et al. (1988) |
| | CYP2A3 | IIA3 | a3 | Rat | R | Kimura, S. et al. (1989) |
| | | | 15α | Mouse | R | Squires and Negishi (1988) |
| | | | P450(1) | Human | R | Phillips et al. (1985a) |

TABLE 1-continued
P450 Genes and Their Products

|  |  |  | IIA3 | Human | R | Yamano, S. et al. |
|---|---|---|---|---|---|---|
| IIB | CYP2B1 | IIB1 | b | Rat | R | Fujii-Kuriyama et al. (1982) |
|  |  |  |  |  | R | Gotoh et al. (1983) |
|  |  |  |  |  | P | Yuan et al. (1983) |
|  |  |  |  |  | R | Phillips et al. (1983) |
|  |  |  |  |  | R | Affolter and Anderson (1984) |

| Family | Locus symbol | Protein name | | Species and Trivial name | Source[a] Reference | |
|---|---|---|---|---|---|---|
|  | CYP2B2 | IB2 | c | Rat | R | Fujii-Kuriyama et al. (1982) |
|  |  |  |  |  | D | Mizukami et al. (1983) |
|  |  |  |  |  | P | Yuan et al. (1983) |
|  |  |  |  |  | R | Phillips et al. (1983) |
|  |  |  |  |  | R | Affolter and Anderson (1984) |
|  | CYP2B3 | IIB3 | IIB3 | Rat | R | Labbë et al. (1988) |
|  | CYP2B4 | IIB4 | LM2 | Rabbit | P | Heinemann and Ozois (1983) |
|  |  |  |  |  | P | Tarr et al. (1983) |
|  |  |  | p54 |  | R | Komori et al. (1988) |
|  |  |  | B0 |  | R | Gasser et al. (1988) |
|  |  |  | P-450$_1$, b15 |  | R | Komori et al. (1988) |
|  |  |  | B1 |  | R | Gasser et al. (1988) |
|  |  |  | b46 |  | R | Komori et al. (1988) |
|  | CYP2B4P |  | (pseudogene) | Rabbit | D | Zaphiropoulos et al. (1986) |
|  | CYP2B5 | IIB5 | b52 | Rabbit | R | Komori et al. (1988) |
|  |  |  | B2 |  | R | Gasser et al. (1988) |
|  |  |  | HP1 |  | R | Komori et al. (1988) |
|  | CYP2B6 | IIB6 | LM2 | Human | R | Miles et al. (1988) |
|  | CYP2B7 | IIB7 |  | Human | R | Yamano, S. et al. |
|  | CYP2B8 | IIB8 |  | Human | R | Yamano, S. et al. |
|  | CYP2B9 | IIB9 | pf26 | Mouse | R | Noshiro et al. (1988) |
|  | CYP2B10 | IIB10 | pf3/46 | Mouse | R | Noshiro et al. (1988) |
| IIC | CYP2C1 | IIC1 | PBc1 | Rabbit | R | Leighton et al. (1984) |
|  | CYP2C2 | IIC2 | PBc2, K | Rabbit | R | Leighton et al. (1984) |
|  |  |  |  |  | D | Govind et al. (1986) |
|  |  |  | PHP2 |  | R | Imai et al. (1988) |
|  | CYP2C3 | IIC3 | PBc3 | Rabbit | R | Leighton et al. (1984) |
|  |  |  | 3b |  | P | Ozols et al. (1985) |
|  | CYP2C4 | IIC4 | 1-88 | Rabbit | R | Johnson et al. (1987) |
|  |  |  | PBc4 |  | R | Zhao et al. (1987) |
|  | CYP2C5 | IIC5 | form 1 | Rabbit | R | Tukey et al. (1985) |
|  | CYP2C6 | IIC6 | PB1 | Rat | R | Gonzalez et al. (1986a) |
|  |  |  | pTF2 |  | R | Friedberg et al. (1986) |
|  |  |  |  |  | R | Kimura, H. et al. (1988) |
|  | CYP2C6P | (pseudogene) |  | Rat | R | Kimura, H. et al. (1986) |
|  | CYP2C7 | IIC7 | f | Rat | R | Gonzalez et al. (1986a) |
|  |  |  | pTF1 |  | R | Friedberg et al. (1986) |
|  | CYP2C8 | IIC8 | form 1 | Human | R | Okino et al. (1987) |
|  |  |  | IIC2 |  | R | Kimura, S. et al. (1987a) |
|  |  |  | mp-12, mp-20 | Human | R | Ged et al. (1988) |
|  | CYP2C9 | IIC9 | IIC1 | Human | R | Kimura, S. et al. (1987a) |
|  |  |  |  |  | R | Yasumori et al. (1987) |
|  |  |  |  |  | R | Meehan et al. (1988a) |
|  |  |  | mp-4 |  | R | Ged et al. (1988) |
|  | CYP2C10 | IIC10 | mp | Human | R | Umbehauer et al. (1987) |
|  |  |  | mp-8 | Human | R | Get et al. (1988) |
|  | CYP2C11 | IIC11 | h, M-1, 16α | Rat | R | Yoshioka et al. (1987) |
|  |  |  |  |  | D | Morishima et al. (1987) |
|  |  |  |  |  | R | Zaphiropoulos et al. (1988) |
|  | CYP2C12 | IIC12 | i, 15β | Rat | R | Zaphiropoulos et al. (1988) |
|  | CYP2C13 | IIC13 | g | Rat | R | McClellan-Green et al. (1988) |
|  | CYP2C14 | IIC14 | pHP3 | Rabbit | R | Imai (1987) |
|  | CYP2C15 | IIC15 | b32-3 | Rabbit | R | Imai et al. (1987) |
|  | CYP2D1 | IID1 | db1 | Rat | R | Gonzalez et al. (1987) |
|  |  |  | CMF2 | Rat | R | Ishida et al. (1988b) |
|  | CYP2D2 | IID2 | db2 | Rat | R | Gonzalez et al. (1987) |
|  |  |  | CMF2 | Rat | R | Ishida et al. (1988b) |
|  | CYP2D3 | IID3 | db3 | Rat | R | Matsunaga, E. et al. |
|  | CYP2D4 | IID4 | db4 | Rat | R | Matsunaga, E. et al. |
|  |  |  | CMF3 | Rat | R | Ishida et al. (1988b) |
|  | CYP2D5 | IID5 | db5 | Rat | R | Matsunaga, E. et al. |
|  |  |  | CMF1b | Rat | R | Ishida et al. (1988b) |
|  | CYP2D6 | IID6 | db1 | Human | R | Gonzalez et al. (1988b) |
|  |  |  |  |  | R | Gonzalez et al. (1988c) |
|  | CYP2D7 | IID7 |  | Human | D | Kimura, S. et al. |
|  | CYP2D8 | IID8 |  | Human | D | Kimura, S. et al. |
|  | CYP2D9 | IID9 | 16α | Mouse | R | Wong et al. (1987) |
|  | CYP2D10 | IID10 | cb | Mouse | R | Ichikawa et al. (1989) |
| IIE | CYP2E1 | IIE1 | j | Human | R | Song et al. (1986) |
|  |  |  |  |  | D | Umeno et al. (1988a) |
|  |  |  |  | Rat | R | Song et al. (1986) |
|  |  |  |  |  | D | Umeno et al. (1988b) |

TABLE 1-continued

P450 Genes and Their Products

| | | | | | | |
|---|---|---|---|---|---|---|
| | | | 3a | Rabbit | R | Khani et al. (1987) |
| | | | | | R | Imai et al. (1988) |
| | | | | | D | Khani et al. (1988) |
| | CYP2E2 | IIE2 | IIE2 | Rabbit | D | Khani et al. (1988) |
| IIF | CYP2F1 | IIF1 | | Human | R | Nhamburo et al. |
| IIG | CYP2G1 | IIG1 | olf1 | Rat | R | Nef et al. (1989) |
| IIH | CYP2H1 | IIH1 | PB15 | Chicken | R | Hobbs et al. (1986) |
| IIIA | CYP3A1 | IIIA1 | pcn1 | Rat | R | Gonzalez et al. (1985) |
| | CYP3A2 | IIIA2 | pcn2 | Rat | R | Gonzalez et al. (1986b) |
| | CYP3A3 | IIIA3 | HLp | Human | R | Molowa et al. (1986) |
| | CYP3A4 | IIIA4 | nf-25 | Human | R | Beaune et al. (1986) |
| | | | pcn1 | | R | Gonzalez et al. (1988a) |
| | | | nf-10 | | R | Bork et al. (1989) |
| | CYP3A5 | IIIA5 | pcn3 | Human | R | Aoyama, T. et al. |
| | CYP3A6 | IIIA6 | 3c | Rabbit | R | Dalet et al. (1988) |
| IVA | CYP4A1 | IVA1 | LAω 1 | Rat | R | Hardwick et al. (1987) |
| | CYP4A2 | IVA2 | LAω 2 | Rat | R | Kimura, S. et al. |
| | CYP4A3 | IVA3 | LAω 3 | Rat | D | Kumara, S. et al. |
| | CYP4A4 | IVA4 | p-2 | Rabbit | R | Matsubara et al. (1987) |
| | CYP4A5 | IVA5 | LAω 1 | Rabbit | R | Johnson, E. F. et al. |
| | CYP4A6 | IVA6 | LAω 2 | Rabbit | R | Johnson, E. F. et al. |
| | CYP4A7 | IVA7 | LAω 3 | Rabbit | R | Johnson, E. F. et al. |
| IVB | CYP4B1 | IVB1 | Lung P450 | Human | R | Nhamburo et al. |
| | | | form 5 | Rat | R | R. Gasser and R. M. Philpot |
| | | | form 5 | Rabbit | R | R. Gasser and R. M. Philpot |
| VIA | CYP6A1 | VIA1 | | House fly | R | Feyereisen, R. et al. (1989) |
| XIA | CYP11A1 | XIA1 | scc | Human | R | Chung et al. (1986b) |
| | | | | | D | Morohashi et al. (1987a) |
| | | | | Cow | R | Morohashi et al. (1984) |
| | | | | | P | Chashchin et al. (1986) |
| XIB | CYP11B1 | XIB1 | 11β | Cow | R | Chua et al. (1987) |
| | | | | | R | Morohashi et al. (1987b) |
| XVII | CYP17 | XVIIA1 | 17α | Cow | R | Zuber et al. (1986) |
| | | | | Human | R | Chung et al. (1987) |
| | | | | | D | Picado-Leonard and Miller (1987) |
| | | | | | R | Bradshaw et al. (1987) |
| | | | | | D | Kagimoto et al. (1988) |
| | | | | Pig | R | Chung et al. (1987) |
| | | | | Rat | R | Nishihara et al. (1988) |
| | | | | | R | Namiki et al. (1988) |
| | | | | Chicken | R | Ono et al. (1988) |
| XIX | CYP19 | XIXA1 | arom | Human | R | Simpson et al. (1987) |
| | | | | | R | Chen, S. et al. (1988) |
| | | | | | R | Corbin et al. (1988) |
| | | | | Chicken | R | McPhaul et al. (1988) |
| XXI | CYP21A1 | XXIA1 | c21A | Mouse | C | Chaplin et al. (1986) |
| | | | c21 | Cow | D | Chung et al. (1986a) |
| | | | | | R | John et al. (1986) |
| | | | | | R | Yoshioka et al. (1986) |
| | | | c21 | Pig | P | Haniu et al. (1987) |
| | CYP21A1P | (pseudogene c21A) | | Human | D | Higashi et al. (1986) |
| | | | | | D | White et al. (1986) |
| | CYP21A2 | XXIA2 | c21B | Human | D | Higashi et al. (1986) |
| | | | | | D | White et al. (1986) |
| | | | | | R | Matteson et al. (1987) |
| | CYP21A2P | (pseudogene c21B) | | Mouse | D | Chaplin et al. (1986) |
| XXVI | CYP26 | XXVIA1 | 26-ohp | Rabbit | R | Anderson, S. et al. |
| | CYP51 | P450LI | 14DM | S. cerevisiae | D | Kalb et al. (1987) |
| | | | | C. tropicalis | D | Chen, C. et al. (1988) |
| | CYP52 | P450LII | alk | C. tropicalis | D | Sanglard and Loper (1989) |
| | CYP101 | P450CI | cam | Ps. putida | P | Haniu et al. (1982) |
| | | | | | D | Unger et al. (1986) |
| | CYP102 | P450CII | BM-3 | B. megaterium | D | Ruettinger, R. T. et al. | aD, DNA; R, CDNA derived from RNA; P, protein sequence.

A surprising aspect of the present invention is the finding that, at least in the case of *E. coli*, the host bacterial organism produces an electron-donating capability that can substitute for mammalian cytochrome P450 reductase function. However, it may be the case that for certain P450s or certain bacterial expression hosts, one will desire to co-express a mammalian P450 reductase or other compatible reductase molecule. This would be achieved by cloning the cDNA for the reductase into an expression plasmid carrying an antibiotic resistance marker distinct from that carried by the pCWmod17 plasmid so that both expression plasmids may replicate in the same *E. coli* cell. Rat liver NADPH-cytochrome P450 reductase has been expressed previously in *E. coli* (Porter et al., 1987). The reductase coding sequence will be placed downstream of an appropriate *E. coli* promoter(s), ribosome binding site and spacer region in the plasmid expression vector using standard molecular cloning techniques.

It is proposed that the reductase molecule need not be of eukaryotic origin. For example, the as yet unidentified endogenous *E. coli* reductase or the reductase moiety of P450 BM-3 (of *Bacillus megaterium*) may also serve as electron donors for the bacterially expressed eukaryotic P450. Furthermore, the cloned reductase expression unit need not be on a separate plasmid distinct from the pCWmod17 plasmid. A suitable location may be found on the pCWmod17 plasmid where the reductase expression unit may be appropriately placed such that both the P450 and reductase cDNAs will reside on the same plasmid. Alternatively, the reductase expression unit can be incorporated into the E. coli chromosome via phage mediated transduction or lysogeny.

The inventor also believes that the growth conditions of the E. coli are of paramount importance for active and high level bacterial expression of cytochrome P450 enzymes. For example, growth of cells in standard Luria Broth gives a very low yield of expressed protein. Moreover, growth of cells in Luria Broth or TB media at the standard optimal growth temperature of 37° C. yields significant levels of expressed enzyme, but the cells show no characteristic absorption at 450 nm when in the reduced and carbon monoxide bound state (indicating that the enzyme is produced but is in an inactive state). Additionally, different bacterial strains show marked differences in their ability to produce the enzyme. Thus, it seems clear that factors other than the expression plasmid and the cDNA are important in the production of active enzyme in large quantities.

The following Examples are included to demonstrate preferred modes for the practice of the present invention. Those of skill in the art will appreciate, in light of the present disclosure and their general familiarity with associated technical methodologies, that modifications and variations may be employed without departing from the spirit and scope of the invention.

EXAMPLE I

Expression of Biologically Active Cytochrome P450$_{17\alpha}$ in E. coli

In the present Example, the cDNA encoding bovine 17α-hydroxylase (P450$_{17\alpha}$) was employed to demonstrate the utility of E. coli as an expression system for eukaryotic P450s. This microsomal P450 catalyzes the regio- and stereospecific 17α-hydroxylation of the C21-steroids pregnenolone and progesterone in the pathway leading to the production of cortisol in the adrenal cortex of most mammalian species. P450$_{17\alpha}$ also converts these 17α-hydroxylated products to the C19-androgen precursors of sex hormones via the 17,20-lyase reaction in the gonads of all species of mammals. P450$_{17\alpha}$ (product of the CYP17 μgene (Nebert et al., 1989)) is a typical representative of the large number of microsomal P450 enzymes and it is expected that the techniques employed in connection with the bacterial expression of this specific P450 will be generally applicable.

In order to express this P450 in bacteria, the cDNA for the coding region of bovine P450$_{17\alpha}$ (Zuber et al., 1986) was cloned into the E. coli expression vector pCW, a derivative of pHSe5 (Muchmore et al., 1989), containing two tac promoter cassettes (Pharmacia #27-4883-01) upstream of Nde 1 (CATATG) restriction enzyme cloning site coincident with the initiation ATG codon. This vector also contained a strong trp A transcription terminator sequence and the Iac I$^q$ gene encoding the lac repressor molecule which prevents transcription from the tac promoters prior to addition of the inducer IPTG. Upon transformation of this expression plasmid containing the native codons of P450$_{17\alpha}$ into the E. coli strain JM109, no immunoreactive P450 protein was produced following derepression of the tac promoters.

Figures 2A, 2B:
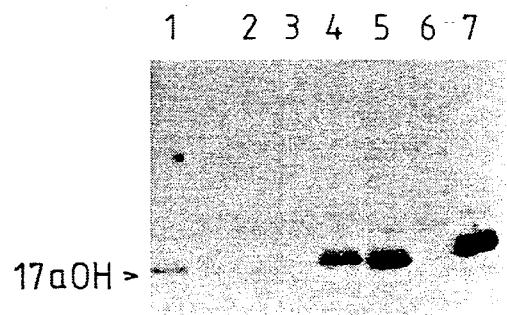
FIGS. 2A and B Nucleotide and amino acid sequences at the 5'-ends of native (nat17) and modified (mod17) $P450_{17\alpha}$ cDNAs and their expression in $E.$ $coli$
FIG. 2(B) is an immunoblot analysis of bacterially expressed 17α hydroxylase. Lane 1, 9.4 μg of bovine adrenocortical microsomes; lane 2, 50 μg of total cell protein (TCP) JM109 (pCWnat17) +IPTG; lane 3, 50 μg TCP JM109 (pCWmod17) −IPTG; lane 4, 50 μg TCP JM109 (pCWmod17) +IPTG; lane 5, a mixture of samples shown in lanes 6 and 7; lanes 6 and 7, the 225,000 xg supernatant and pellet fractions from a 200 μl culture of JM109 (pCWmod17) +IPTG, respectively.

Examination of the amino terminal coding sequence of P450$_{17}$, based on the reports by others that this region may play an important role in expression levels in E. coli, led to the introduction of modifications into the cDNA by PCR mutagenesis as indicated in FIG. 2A in an attempt to optimize parameters for the bacterial expression. Specifically, the native second codon was changed from TGG (Trp) to GCT (Ala) a preferred second codon for expression of Iac Z (Looman et al., 1987), and codons 4 and 5 were changed to TTA (silent mutations) since this region of E. coli mRNAs has been shown to be rich in A and U nucleotides (Stormo et al., 1982). Also the last nucleotide of codons 6 and 7 were changed to A and T respectively (silent mutations) to minimize secondary structure formation in the messenger RNA (Scharder et al., 1989).

The nucleotide changes (indicated in bold letters in FIG. 2 A) were introduced by means of PCR mutagenesis (Higuchi et al., 1988), amplifying the sequences between the ATG initiator codon and a unique EcoRI restriction site of the plasmid pCD17α-2 (Zuber et al., 1986). Following sequencing of the amplification products, the expression plasmids were constructed by the simultaneous ligation of NdeI/HindIII cleaved pCW vector DNA with a 1257 bp EcoRI fragment containing the native or modified cDNA PCR fragments encoding amino acids 1-91. The final pCW expression plasmids (pCWnat17 and pCWmod17) were subjected to diagnostic restriction enzyme analysis prior to transformation into E. coli.

Immunoblot analysis (FIG. 2B) indicated that these alterations had a profound effect on expression of P450$_{17\alpha}$ in E. coli and that this expression was efficiently repressed in the absence of IPTG. Fractionation of transformed E. coli into membranes and cytosol (Osborne et al., 1974) established that the expressed P450$_{17\alpha}$ was associated with the membranes. JM109 cells harboring the P450$_{17\alpha}$ expression plasmids were grown to an OD$_{550}$=0.4–0.8 in TB broth containing 50–100 μg/ml ampicillin at 37° C. (FIG. 2B). Where indicated, induction of the tac promoters was initiated by 1mM IPTG. The cells were shifted to 28° C. and gently shaken for 48 hrs, pelleted, washed once in MOPS buffer (50 mM MOPS pH=7.5, 100 mM KCl, 1mM EDTA, 1mM DTT) and resuspended in the same buffer (1/20 volume of the original culture). Lysozyme was added to a final concentration of 0.2 mg/ml and the cells were incubated on ice for 30 min. PMSF, leupeptin and aprotinin were added to final concentrations of 1 mM, 0.1 μg/ml and 0.04 U/ml respectively, and the resulting sheroplasts were lysed by sonication in a salt ice bath. Unbroken cells and debris were pelleted at 1,200 xg for 10 min. MgCl$_2$ (6 mM) was added to the supernatant which was centrifuged at 225,000 xg for 30 minutes at 4° C. The resultant membrane pellet was resuspended in MOPS buffer containing 6 mM MgCl$_2$ by gentle homogenization and recentrifuged at 225,000 xg as before. Following centrifugation this washed membrane pellet was resuspended in MOPS buffer. TCP was prepared by boiling cells in 62.5 mM Tris-HCl (pH=6.8) containing 2% SDS. Samples were fractionated on 8% SDS-polyacrylamide gels and transferred to nitrocellulose membranes for immunoblot analysis (Zuber et al., 1985).

Figure 3A:
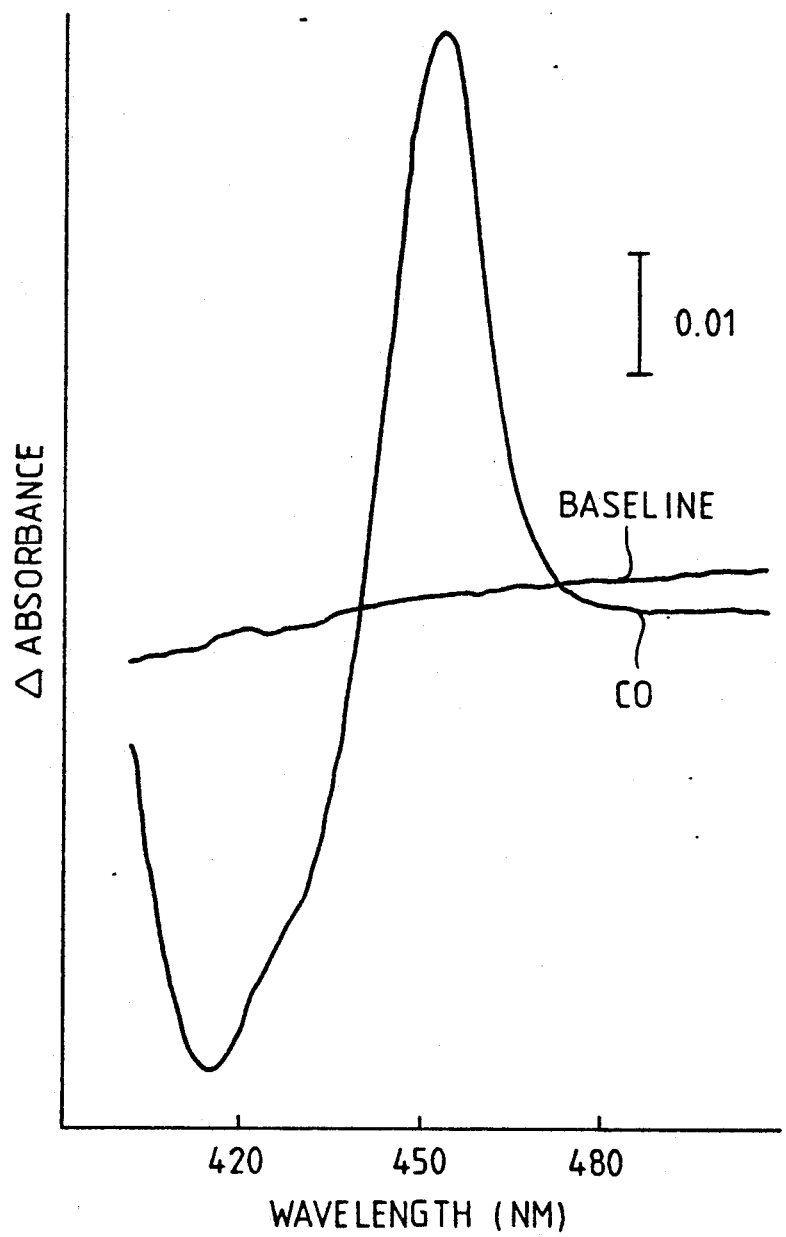
FIGS. 3A and B Reduced CO-difference spectrum (A) and substrate binding spectra (B) of $P450_{17\alpha}$ in intact $E.$ $coli$ cells. A representative baseline tracing recorded from 350 to 510 nm is shown. Also shown are spectra obtained when aliquots of steroids and ethanol were added until bacterially expressed $P450_{17\alpha}$ was spectrally saturated.

Not only was the P450$_{17\alpha}$ protein expressed in *E. coli*, this protein was found to have the spectral characteristics of functional P450$_{17\alpha}$ (FIG. 3A). The reduced CO-difference spectrum obtained in intact *E. coli* showed the characteristic 450 nm absorbance maximum of all cytochromes P450 (Omura et al., 1962). In these studies, 200 ml of JM109 harboring pCWmod17 were cultured and induced as described above for the FIG. 2 studies. Cells were washed and resuspended in 10ml MOPS buffer. A 0.5 ml aliquot of concentrated cells was diluted with 5.5 ml of MOPS buffer containing 10mM glucose and divided equally between two cuvettes. Several grains of sodium dithionite were added to each cuvette and the baseline reduced difference spectrum was recorded in an Aminco DW-2A spectrophotometer. Carbon monoxide was then bubbled through the sample cuvette and the reduced-CO bound difference spectrum was recorded.

Figures 1, 3B:
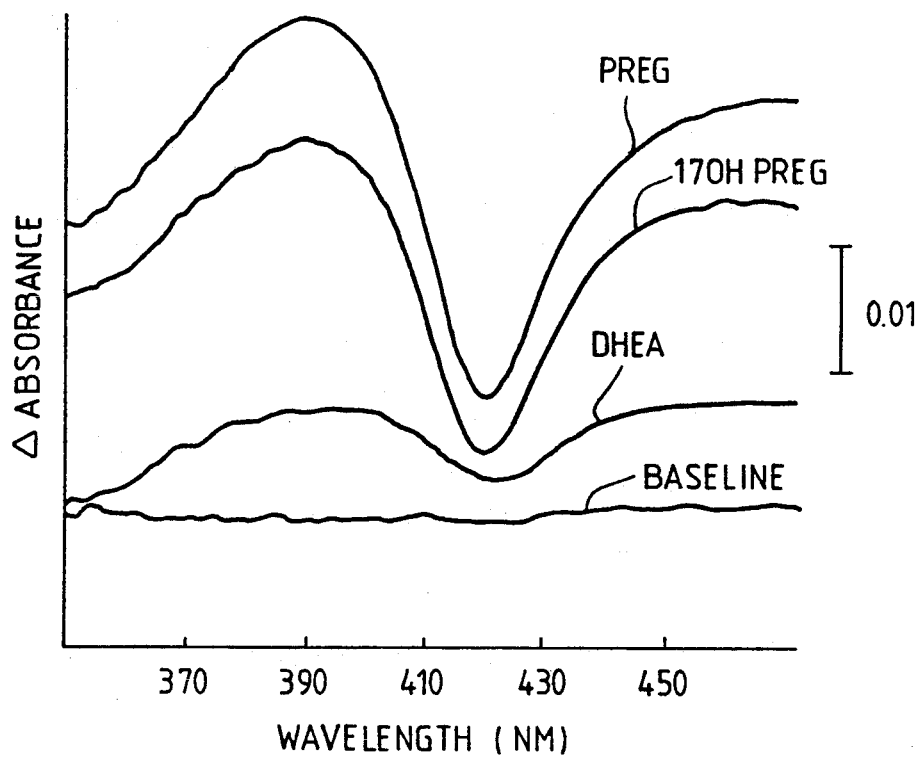
Figures 2, 3B:
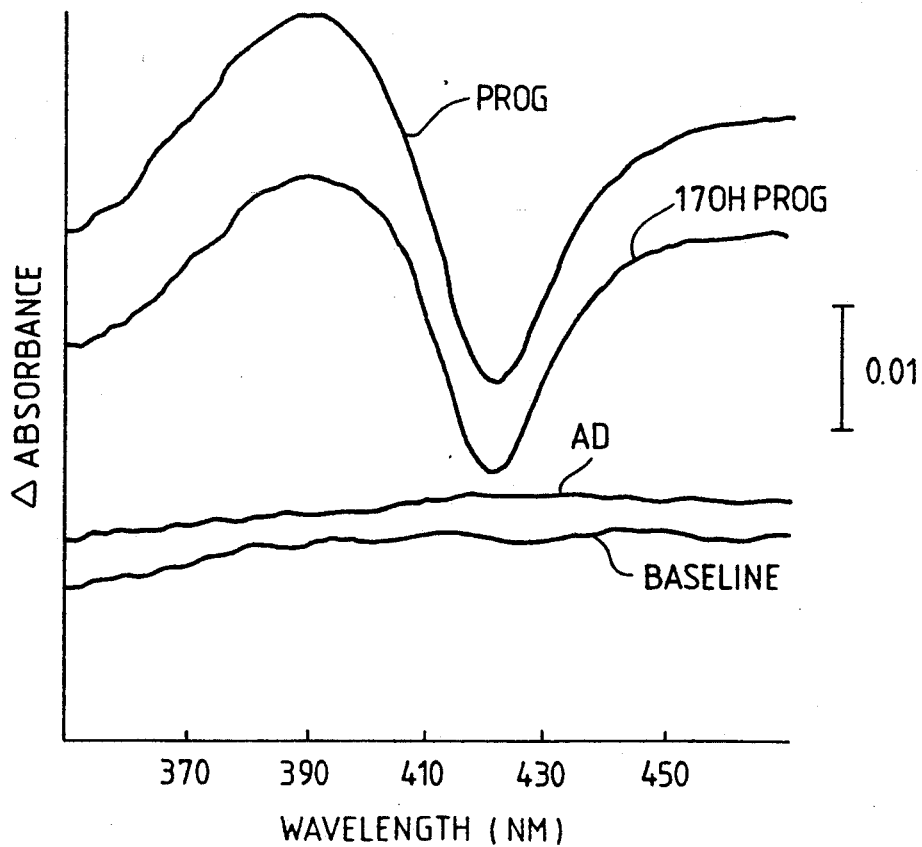

As shown in FIG. 3B, binding of substrates was also observed by detection of substrate-induced difference spectra (Narasimhulu et al., 1965) in intact bacteria following addition of the C21 steroids pregnenolone, progesterone, 17$\alpha$-hydroxyregnenolone or 17$\alpha$-hydroxyprogesterone. The C19 steroid product of the 17,20-lyase reaction, dehydroepiandrosterone, showed much less binding while another C19 steroid, androstenedione which is not a product of bovine 17,20-lyase, showed no binding. The functional role of the binding of C21 steroids to the expressed P450$_{17\alpha}$ was determined by incubation of transformed *E. coli* with radiolabeled substrates and HPLC analysis of substrates and products.

For the studies shown in FIG. 3B, substrate binding spectra were obtained by adding steroid to the indicated final concentration: (preg) pregnenolone 22 $\mu$M, (170H preg) 17$\alpha$-hydroxypregnenolone 40 $\mu$M, (DHEA) dihydroepiandrosterone 46 $\mu$M, (AD) androstenedione 46 $\mu$M. A volume of washed cells containing 1.6 nmoles p450$_{17\alpha}$ was diluted to 6 ml with MOPS buffer and divided into the sample and reference cuvettes of an Aminco DW-2A spectrophotometer. A baseline tracing was recorded from 350 to 510 nm (representative shown). Steroid was added in 10 $\mu$l aliquots (1-2 mg/ml in ethanol) to the sample with an equal volume of ethanol added to the reference. Additional aliquots of steroids and ethanol were added until the bacterially expressed P450$_{17\alpha}$ was spectrally saturated (spectra shown).

Figure 4A:
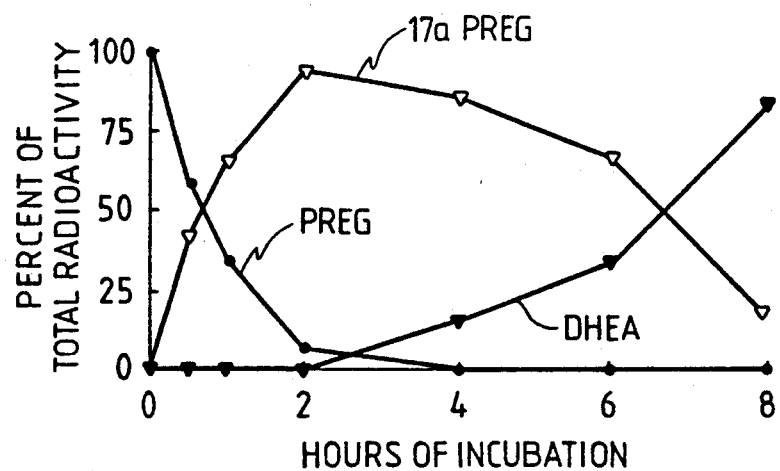
FIG. 4 Steroid metabolism by bacterially expressed bovine 17α-hydroxylase in intact $E.$ $coli.$ Initial substrates were pregnenolone, 17α-hydroxypregnenolone, and progesterone.
Figure 4B:
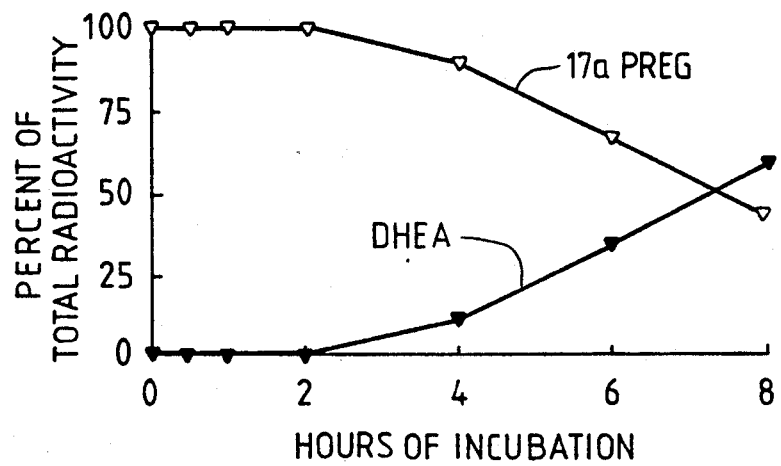
Figure 4C:
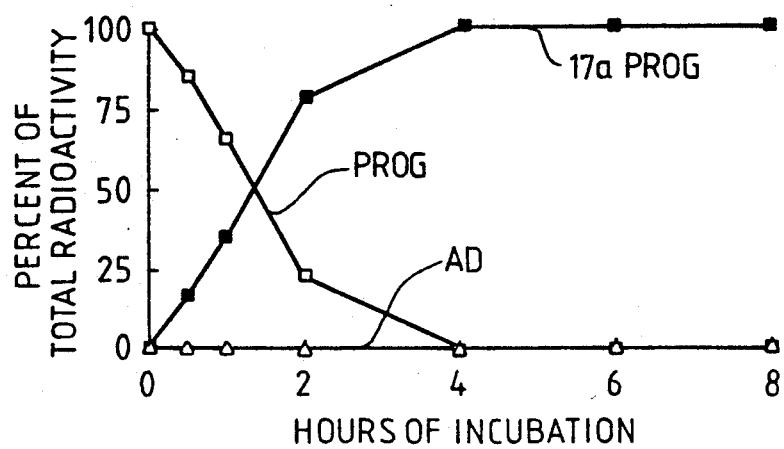

FIG. 4 demonstrates steroid metabolism by bacterially expressed bovine 17$\alpha$-hydroxylase in intact *E. coli*. The initial substrates employed were pregnenolone, 17$\alpha$-hydroxypregnenolone, and progesterone. For these studies, *E. coli* were grown and induced as described for the FIG. 2 studies. Cells were pelleted, washed once in MOPS buffer and resuspended in the same buffer at 1/20 volume of the original bacterial culture. A volume of concentrated cells corresponding to 3.7-4.2 nmoles P450$_{17\alpha}$ was diluted to 5 ml MOPS buffer containing 10 mM glucose, 2.5 $\mu$M steroid and 100,000 cpm/ml of H-labeled radioactive steroid. Samples were incubated at 28° C. with gentle shaking. Aliquots (0.5 ml) were removed at 0, 0.5, 1, 2, 4, 6 and 8 hours after steroid addition. Following extraction of cells and culture media steroids were analyzed by HPLC as previously described (Estabrook et al., 1988). Addition of glucose was not required for metabolism, no significant levels of additional steroid products were observed and ketoconazole, a P450 specific inhibitor (Loose et al., 1983), was found to inhibit 17$\alpha$-hydroxylase activity.

The enzymatic profile (FIG. 4) of the expressed P450$_{17\alpha}$ in bacteria was the same as observed in other heterologous systems, COS 1 cells (Estabrook et al, 1988) and yeast (Sakaki et al., 1988). Briefly, pregnenolone and progesterone were readily converted to their 17$\alpha$-hydroxylated products and 17$\alpha$-hydroxyprogesterone was not converted to androstenedione. Furthermore, when pregnenolone was added as substrate it is first converted almost entirely to 17$\alpha$-hydroxypregnenolone before 17,20-lyase metabolism occurs. A similar pattern of metabolism is also observed upon expression in COS 1 cells (Estabrook et al., 1988). Consequently bovine P450$_{17\alpha}$ expressed in *E. coli* was indistinguishable from that expressed in monkey kidney cells or yeast.

Surprisingly, *E. coli* were capable of supporting the enzymatic activities of P450$_{17\alpha}$ (FIG. 4) without added cytochrome P450 reductase. The flavoprotein, NADPH-cytochrome P450 reductase, is a ubiquitous enzyme in eukaryotic cells which is generally required to support the activity of microsomal P450s. Furthermore P450 reductase from one species is able to support the activity of P450s from other species However, the presence of this enzyme in *E. coli* has not been detected immunologically (Porter et al., 1987). A unique form of cytochrome P450 in *B. megaterium* (P450$_{BM3}$) is found to be a fusion protein between the P450 and a flavoprotein which resembles the eukaryotic P450 reductase in primary sequence, by binding both FAD and FMN and by utilizing NADPH as a source of reducing equivalents (18, 19). Also, NADPH-sulfite reductase in S. timurum and *E. coli* is a bacterial flavoprotein reported to have properties similar to P450 reductase (Ostrowski et al., 1989). Perhaps sulfite reductase or another *E. coli* flavoprotein is able to transfer electrons to P450$_{17\alpha}$ localized in the bacterial cell membranes to support these hydroxylation reactions. The present inventor has observed in vitro that 17$\alpha$-hydroxylase activity can only be reconstituted by mixing membranes and the soluble fraction from transformed *E. coli*, and is not present in either fraction alone.

These results establish for the first time that a eukaryotic P450 can be expressed in bacteria such as *E. coli* in a functional form and that strain JM109 is able to support all the known activities of bovine P450$_{17\alpha}$ leading to metabolic profiles indistinguishable from those observed in eukaryotic cells. Consequently, by altering sequences within the first seven codons of the bovine P450$_{17\alpha}$ cDNA to optimize for expression in *E. coli*, a bacterial expression system has been obtained.

EXAMPLE II

Preferred Growth Conditions

The following have shown to be optimal conditions for the production of P450$_{17\alpha}$ in *E. coli*.

The starting material is a colony of *E. coli* strain JM 109 transformed with the plasmid pCWmod17 $\mu$grown overnight at 37° C. on an LB (Luria Broth) plate (10g Bacto-Tryptone; 5 $\mu$g Bacto-Yeast Extract; 5 $\mu$g NaCl; 15 $\mu$g Bacto-Agar per liter of H$_2$O) containing 50 $\mu$g/ml ampicillin. A single isolated colony is streaked out on a fresh LB Amp plate and grown overnight at 37° C. A single isolated colony from this plate is placed in several ml of LB Amp media (same as above minus Bacto-agar) and grown with vigorous shaking until the culture media reaches an OD$_{600}$ of 0.3. Sterile glycerol is added to this culture for a final concentration of 20%. These cells are frozen at −70° C. in 1 ml aliquots and will serve as inoculum for future experiments.

The standard expression protocol is as follows. Three to five ml of LB AMp media is seeded with several microfilters of thawd innoculmn. This culture is grown overnight with vigorous shaking at 37° C. This intermediate culture is diluted 1/200 into TB media (24 μg/l Bacto-Yeast Extract; 12 g/l Bacto Tryptone; 0.4% Glycerol; 17 mM KH$_2$PO$_4$; 72 mM K$_2$HPO$_4$ (Phosphate added after autoclaving from a 10 fold concentrated stock) containing 50 μg/ml ampicillin. Typically a 500 ml Erlenmeyer flask will contain 50 to 200 ml of media. This innoculated culture is then incubated at 37° C. with vigorous shaking until the OD$_{600}$ of the media is 0.4 to 0.8. At this time the culture is removed and allowed to cool to below 30° C. At this point IPTG (isopropyl-β-D-thiogalactopyranoside) is added from a 100 mM stock for a final concentration of I mM. The culture is then transferred to a 30° C. incubator and gently shaken for 48 to 60 hours at which point the level of P450 production is maximal.

Although these conditions have proved adequate to produce bovine 17α-hydroxylase in E. coli several possible adjuvants may lead to improvements in the overall yield. These include but are not limited to the following. Addition of metal salts (Fe, Na, Mg, Mn, Mo etc.), amino acids, glucose and vitamins to the culture media may lead to improved yields especially since strain JM 109 may be impaired in its ability to synthesize the amino acid proline and the vitamin thiamine when grown under the conditions listed above. Another type of media supplement that may improve the production of P450s in bacteria are heme or heme precursors (glutamate or 5-aminolevulinic acid). Since P450s are hemoproteins the synthesis of heme in bacteria may become limited if large amounts of P450 are being synthesized in the cell. Thus, addition of these compounds may counteract this possible limitation.

It may also prove beneficial to add additional aliquots of IPTG to the media during the growth of the culture to insure a proper amount of this inducing agent throughout the long incubation period. Finally, the control of pH and dissolved oxygen in the culture can have a dramatic affect on cell viability and yield of recombinant protein. These parameters are most easily controlled in chemostat culture although the use of alternative buffering agents may suffice to control pH in batch culture. Oxygen tension may be an important parameter since others have reported that high O$_2$ concentrations are deleterious to the stability of 17α-hydroxylase in eukaryotic cells.

EXAMPLE III

Expression of Other Cytochrome P450s in E. coli

The expression of bovine mitochondrial cholesterol side chain cleavage (SCC) enzyme as well as human liver microsomal P450 IIIA4 nifedipine oxidase has now also been expressed in E. coli.

For expression of SCC, the pTRC 99A vector containing a trc promoter and lac ribosome binding site and spacer region was utilized. This protein is synthesized in eukaryotes in a precursor from which undergoes post translational proteolytic cleavage of the first 39 amino acid residues to form the mature enzyme. An attempt was made to produce both of these forms in E. coli. The nucleotide and amino terminal amino acid sequences of these constructs are set forth below. (bold lettering indicates alteration of the native sequences numbers refer to the amino acid sequences of the precursor protein)

precursor:
ATG GTA GCA AGG GGG CTT CCC CTG CGC TCA GCC CTG GTC AAA GCC TGC CCA CCC ATC
Met Val Ala Arg Gly Leu Pro Leu Arg Ser Ala Leu Val Lys Ala Cys Pro Pro Ile
1   1   3   4   5   6   7   8   9   10  11  12  13  14  15  16  17  18  19 mature:
ATG GTC TCC ACA AAG ACC CCT CGC CCC TAC AGT GAG ATC CCC TCC CCT GGT GAC ATT
Met Val Ser Thr Lys Thr Pro Arg Pro Tyr Ser Glu Ile Pro Ser Pro Gly Asp Asn
*   *   41  42  43  44  45  46  47  48  49  50  51  52  53  54  55  56  57

When these sequences were introduced into the pTRC vector, only the mature sequence produced immunoreactive protein as detected in subcellular fractions of these cells. Furthermore, this protein is localized in E. coli membranes, and exhibits a typical reduced CO difference spectra and substrate binding spectra. Initial studies indicated that when the bacterially expressed protein is combined in vitro with the electron transport components of bovine adrenal mitochondria full enzymatic activity is seen. However, other studies indicate that the SCC enzyme is not active in E. coli without exogenous reductase. This result needs to be confirmed but it appears that the endogenous E. coli reductase described earlier can not transfer electrons to mitochondrial P450s. The amount of SCC produced by the pTRC vector is less that the amount of 17α-hydroxylase produced by the pCW vector. Further studies are in progress to introduce the SCC DNAs into the pCW vector with the 5′ nucleotide changes to be important for the bacterial expression of 17α-hydroxylase.

An attempt was also made to express a human liver microsomal P450 IIIA4 (Beaune et al., 1986). The native amino terminal amino acid sequence and corresponding nucleotide sequence is listed below:

ATG GCT CTC ATC CCA GAC TTG GCC ATG GAA ACC TGG CTT CTC CTG GCT GTC AGC CTG
Met Ala Leu Ile Pro Asp Leu Ala Met Glu Thr Trp Leu Leu Leu Ala Val Ser Leu

In these studies, an emphasis was placed on the conservation of the native amino acid sequence and the pCW vector was used throughout. In the initial studies the following nucleotide sequences were introduced:

```
ATG GCT #T# ATT CCG GAT CTG GCT ATG GAA ACC TGG CTT CTC CTG GCT GTC AGC CTG
Met Ala     Ile Pro Asp Leu Ala Met Glu Thr Trp Leu Leu Leu Ala Val Ser Leu
``` with variable third codons of TTC, TTT, CTT and CTC for a total of four distinct sequences. When these modified cDNAs were introduced into the pCW vector and transformed into *E. coli* no P450 reduced CO difference spectra was observed. It was then noticed that the IIIA4 protein contained several amino acid residues between the N terminal Met residue and its hydrophobic signal peptide (the region underlined above). In most P450s this hydrophobic region follows immediately after the first Met residue. Therefore, the following construction was made which contained the first nine codons of the modified 17α-hydroxylase cDNA attached at the 21st codon of IIIA4 i.e., (caps IIIA4, lower case 17αOH)

expressing these enzymes in *E. coli*. The deletion of codons corresponding to amino acid residues between the initiation Met and the hydrophobic signal sequences may be necessary in some cases. Studies are in progress to express aromatase and C21 hydroxylase P450s using these guidelines. Aromatase enzyme contains the above mentioned extra peptide sequences while C21 does not.

While the compositions and methods of this invention have been described in terms of preferred embodiments, it will be apparent to those of skill in the art that variations may be applied to the compositions, methods, and in the steps or in the sequence of steps of the methods described herein without departing from the concept, spirit and scope of the invention. More specifically, it

```
atg gct ctg tta tta gca gtt ttt ctg GTG CTC CTC TAT CTA TAT GGA ACC CAT TCA
met ala leu leu leu ala val phe leu Val Leu Leu Tyr Leu Tyr Gly Thr His Ser
```

When this cDNA in plasmid pCW was introduced into *E. coli* a characteristic P450 CO difference spectra was observed in these cells indicating high level production of active nifedipine oxidase P450 enzyme.

From these data it appears that the substitution of the first 10 or so codons of the modified 17α-hydroxylase cDNA sequence for the corresponding codons of another P450 cDNA may be the most efficient method of will apparent that certain agents which are both chemically and physiologically related may be substituted for the agents described herein while the same or similar results would be achieved. All sets of similar substitutes and modifications apparent to those skilled in the art in light of the present disclosure are deemed to be within the spirit, scope, and concept of the invention as defined by the appended claims.

---

What is claimed is:

1. A stably transformed bacterial cell of the family Enterobacteriaceae which expresses a biologically active cytochrome P450 enzyme, said transformant comprising a DNA segment consisting essentially of a cytochrome P450 expression construct maintaining host-compatible transcriptional and translational regulatory DNA sequence elements in operable linkage with a eukaryotic cytochrome P450 coding region, said expression construct comprising a transcription promoter, ribosome binding site, spacer region and transcription terminator.

2. The bacterial cell of claim 1, wherein the cytochrome P450 enzyme is a member of the cytochrome P450 I, II, III, IV, VI, XIA, XIB, XVII, XIX, XXI or XXVI family.

3. The bacterial cell of claim 2, wherein the cytochrome P450 enzyme comprises a steroid, fatty acid, prostaglandin, leukotriene, lipid, vitamin, or xenobiotic metabolizing-enzyme.

4. The bacterial cell of claim 3, wherein the cytochrome P450 enzyme is 17α-hydroxylase.

5. The bacterial cell of claim 1, wherein the cytochrome P450 gene is encoded on a plasmid.

6. The bacterial cell of claim 1 wherein the promoter comprises a tac, lac, lac UV5 tac, trc, λP$_L$, T7 or T3 promoter.

7. The bacterial cell of claim 1, wherein the ribosome binding site comprises an E. coli, λ, T7 or T3 ribosome binding site.

8. The bacterial cell of claim 7, wherein the ribosome binding site comprises a T7 μgene 10, or E. coli lac a, lac z, trp A, trp B, trp C, trp D, trp E, trp L, trp R, or trp S ribosome binding site.

9. The bacterial cell of claim 1, wherein the ribosome binding site and spacer region comprise 5'-AGGAGGTCAT- 3'.

10. The bacterial cell of claim 1, wherein the terminator comprises a trp, rrnB, or T7 terminator.

11. The bacterial cell of claim 1, wherein the terminator comprises an RNase III cleavage site.

12. The bacterial cell of claim 10, wherein the bacterial cell is E. coli.

13. The bacterial cell of claim 1, wherein the cytochrome P450 gene comprises a modification to effect improved bacterial expression.

14. The bacterial cell of claim 13, wherein the cytochrome P450 gene comprises a modification in the codon for the second amino acid.

15. The bacterial cell of claim or 5, wherein the codon encoding the second amino acid of the cytochrome P450 enzyme comprises GCT, AAA, ACC, ACT, TAT, AAT, AAC, CAC, CAT, CGT, AGA, CGC, TTT, ATC, ATA, ATT, GTA, TTG, CTT, CTC, TTA, GCC, GCA, GAA, AGC, or AGT.

16. The bacterial cell of claim 15, wherein the codon encoding the second amino acid of the cytochrome P450 enzyme is GCT.

17. The bacterial cell of claim 1 or 14, wherein the codon encoding the fourth or fifth amino acid of said cytochrome P450 enzyme comprises an AT rich codon.

18. The bacterial cell of claim 1 or 14, wherein the first 25 codons of said cytochrome P450 gene comprises not more than two rare codons.

19. The bacterial cell of claim 18, wherein the first 25 codons of said cytochrome P450 gene are devoid of rare codons.

20. The bacterial cell of claim 19, wherein the first 25 codons of said cytochrome P450 gene are devoid of the codons AGA and AGG.

21. The bacterial cell of claim 1, devoid of a eukaryotic cytochrome P450 reductase.

22. The bacterial cell of claim 1, further comprising a eukaryotic cytochrome P450 reductase.

23. A method for the production of a biologically active cytochrome P450 enzyme in a recombinant bacterium comprising preparing a bacterial cell in accordance with anyone of claims 1 through 23 and culturing said cell under condition appropriate to effect expression of the cytochrome P450 enzyme.

24. The method of claim 23, further comprising collecting the cytochrome P450 enzyme so produced.

25. A method for the metabolism of a cytochrome P450 substrate comprising preparing a bacterial cell which expresses a biologically active cytochrome P450 enzyme in accordance with any one of claims 1 through 23, wherein said expressed enzyme is one that is capable of metabolizing said substrate, and subjecting said substrate to the enzyme so produced under conditions effective to metabolize said substrate.

26. The method of claim 25, wherein said enzyme is at least partially purified from said bacterium prior to subjecting the substrate to the enzyme.

27. The method of claim 25, wherein said cytochrome P450 substrate is subjected to bacterial membrane fractions which comprise the enzyme.

28. The method of claim 25 wherein said substrate is a steroid.

29. An isolated DNA segment consisting essentially of a cytochrome P450 expression construct maintaining host-compatible transcriptional and translational regulatory DNA sequence elements in operable linkage with a eukaryotic cytochrome P450 coding region, said expression construct comprising a transcription promoter, ribosome binding site, spacer region and transcription terminator.

30. The DNA segment of claim 30, wherein the cytochrome P450 enzyme is a member of the cytochrome P450 I, II, III, IV, VI, XIA, XIB, XVII, XIX, XXI or XXVI family.

31. The DNA segment of claim 30, wherein the cytochrome P450 enzyme comprises a steroid, fatty acid, lipid, prostaglandin, leukotriene, vitamin, or xenobiotic metabolizing enzyme.

32. The DNA segment of claim 32, wherein the cytochrome P450 enzyme is a 17α-hydroxylase.

33. The DNA segment of claim 29, further defined as a plasmid.

34. The DNA segment of claim 30, wherein the promoter comprises a tac, lac, lac UV5 tac, trc, λP$_L$, T7 or T3 promoter.

35. The DNA segment of claim 29, wherein the ribosome binding site comprises an E. coli, λ, T7 or T3 ribosome binding site.

36. The DNA segment of claim 35, wherein the ribosome binding site comprises a T7 gene 10, or E. coli lac a, lac z, trp A, trp B, trp C, trp D, trp E, trp L, trp R, or trp S ribosome binding site.

37. The DNA segment of claim 29, wherein the ribosome binding site and spacer region comprise 5'-AGGAGGTCAT- 3'.

38. The DNA segment of claim 29, wherein the terminator comprises a trp, rrnB, or T7 terminator.

39. The DNA segment of claim 29, wherein the terminator comprises an RNase III cleavage site.

40. The DNA segment of claim 29, wherein the cytochrome P450 gene comprises a modification in the codon for the second amino acid.

41. The DNA segment of claim 40, wherein the codon encoding the second amino acid of the cytochrome P450 enzyme comprises GCT, AAA, ACC, ACT, TAT, AAT, AAC, CAC, CAT, CGT, AGA, CGC, TTT, ATC, ATA, ATT, GTA, TTG, CTT, CTC, TTA, GCC, GCA, GAA, AGC, or AGT.

42. The DNA segment of claim 41, wherein the codon encoding the second amino acid of the cytochrome P450 enzyme is GCT.

43. The DNA segment of claim 29, wherein the codon encoding the fourth or fifth amino acid of said cytochrome P450 enzyme comprises an AT rich codon.

44. The DNA segment of claim 29, wherein the first 25 codons of said cytochrome P450 gene comprises not more than two rare codons.

45. The DNA segment of claim 44, wherein the first 25 codons of said cytochrome P450 gene are devoid of rare codons.

46. The DNA segment of claim 29, wherein the first 25 codons of said cytochrome P450 gene are devoid of the codons AGA and AGG.

47. The DNA segment of claim 29, further comprising a cytochrome P450 reductase.

48. A method for obtaining bacterial expression of a biologically active eukaryotic cytochrome P450 enzyme comprising the steps of:
    (a) obtaining a DNA segment which comprises a selected eukaryotic cytochrome P450 enzyme gene;
    (b) modifying the segment so as to operatively combine the gene with a bacterially compatible ribosome binding site, spacer region, transcription terminator and promoter to form a bacterial expression unit;
    (c) transforming bacteria with said bacterial expression unit forming transformant colonies; and
    (d) selecting a transformant colony which expresses said gene in a biologically active manner; and
    (e) culturing said selected transformant under conditions effective to express said eukaryotic cytochrome P450 enzyme.

49. The method of claim 49, wherein said segment is modified by combining said gene with a bacterial expression cassette.

* * * * *

UNITED STATES PATENT AND TRADEMARK OFFICE
CERTIFICATE OF CORRECTION

PATENT NO. : 5,240,831
DATED : August 31, 1993
INVENTOR(S) : Henry J. Barnes

It is certified that error appears in the above-indentified patent and that said Letters Patent is hereby corrected as shown below:

In claim 3, line 46, column 33, delete the hyphen between the words "metabolizing-enzyme".

In claim 4, line 48, column 33, insert "a" before "17a-hydroxylase".

In claim 8, line 58, column 33, delete "µgene" and insert --gene--.

In claim 15, line 35, column 34, delete "or 5" and insert --1 or 14--.

In claim 17, line 44, column 34, delete "14" and insert --13--.

In claim 18, line 47, column 34, delete "14" and insert --13--.

In claim 23, line 63, column 34, delete "23" and insert --22--; and line 64, column 34, delete "condition" and insert --conditions--.

In claim 25, line 6, column 35, delete "23" and insert --22--.

In claim 30, line 26, column 35, delete "30" and insert --29--.

In claim 32, line 35, column 35, delete "32" and insert --31--.

In claim 34, line 39, column 35, delete "30" and insert --29--.

In claim 49, line 49, column 36, delete "49" and

Signed and Sealed this

Nineteenth Day of April, 1994

BRUCE LEHMAN

*Attest:*

*Attesting Officer*                *Commissioner of Patents and Trademarks*

UNITED STATES PATENT AND TRADEMARK OFFICE
CERTIFICATE OF CORRECTION

PATENT NO. : 5,240,831

DATED : August 31, 1993

INVENTOR(S) : Henry J. Barnes

It is certified that error appears in the above-indentified patent and that said Letters Patent is hereby corrected as shown below:

In claim 3, line 46, column 33, delete the hyphen between the words "metabolizing-enzyme".

In claim 4, line 48, column 33, insert "a" before "17a-hydroxylase".

In claim 8, line 58, column 33, delete "µgene" and insert --gene--.

In claim 15, line 35, column 34, delete "or 5" and insert --1 or 14--.

In claim 17, line 44, column 34, delete "14" and insert --13--.

In claim 18, line 47, column 34, delete "14" and insert --13--.

In claim 23, line 63, column 34, delete "23" and insert --22--; and line 64, column 34, delete "condition" and insert --conditions--.

In claim 25, line 6, column 35, delete "23" and insert --22--.

In claim 30, line 26, column 35, delete "30" and insert --29--.

In claim 32, line 35, column 35, delete "32" and insert --31--.

In claim 34, line 39, column 35, delete "30" and insert --29--.

UNITED STATES PATENT AND TRADEMARK OFFICE
CERTIFICATE OF CORRECTION

PATENT NO. : 5,240,831

DATED : August 31, 1993

INVENTOR(S) : Henry J. Barnes

It is certified that error appears in the above-indentified patent and that said Letters Patent is hereby corrected as shown below:

In claim 49, line 49, column 36, delete "49" and insert --48--.

This certificate supersedes Certificate of Correction issued April 19, 1994

Signed and Sealed this

Sixth Day of December, 1994

Attest:

BRUCE LEHMAN

Attesting Officer

Commissioner of Patents and Trademarks